(12) United States Patent
Rank et al.

(10) Patent No.: US 8,518,643 B2
(45) Date of Patent: Aug. 27, 2013

(54) METHOD TO IMPROVE SINGLE MOLECULE ANALYSES

(75) Inventors: David Rank, Pacific Grove, CA (US); Paul Peluso, East Palo Alto, CA (US)

(73) Assignee: Pacific Biosciences of California, Inc., Menlo Park, CA (US)

(*) Notice: Subject to any disclaimer, the term of this patent is extended or adjusted under 35 U.S.C. 154(b) by 319 days.

(21) Appl. No.: 13/018,617

(22) Filed: Feb. 1, 2011

(65) Prior Publication Data
US 2011/0217698 A1  Sep. 8, 2011

Related U.S. Application Data

(60) Provisional application No. 61/301,505, filed on Feb. 4, 2010.

(51) Int. Cl.
| | |
|---|---|
| C12Q 1/68 | (2006.01) |
| C12P 19/34 | (2006.01) |
| C07H 21/02 | (2006.01) |
| C07H 21/04 | (2006.01) |

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 4,711,955 A | 12/1987 | Ward et al. | |
| 5,547,839 A | 8/1996 | Dower et al. | |
| 5,688,648 A | 11/1997 | Mathies et al. | |
| 6,210,896 B1 | 4/2001 | Chan | |
| 6,255,083 B1 | 7/2001 | Williams | |
| 6,399,335 B1 | 6/2002 | Kao et al. | |
| 6,787,308 B2 | 9/2004 | Balasubramanian et al. | |
| 7,041,812 B2 | 5/2006 | Kumar et al. | |
| 7,056,661 B2 | 6/2006 | Korlach et al. | |
| 2003/0044781 A1 | 3/2003 | Korlach et al. | |
| 2003/0077610 A1 | 4/2003 | Nelson et al. | |
| 2003/0096253 A1 | 5/2003 | Nelson et al. | |
| 2003/0162213 A1 | 8/2003 | Fuller et al. | |
| 2003/0190647 A1 | 10/2003 | Odera | |
| 2003/0215862 A1 | 11/2003 | Parce et al. | |
| 2004/0048300 A1 | 3/2004 | Sood et al. | |
| 2004/0152119 A1 | 8/2004 | Sood et al. | |

(Continued)

FOREIGN PATENT DOCUMENTS

| | | |
|---|---|---|
| WO | 91/06678 | 5/1991 |
| WO | 96/27025 | 8/1996 |
| WO | 99/05315 | 2/1999 |

OTHER PUBLICATIONS

Eid, et al., "Real-Time DNA Sequencing from Single Polymerase Molecules," Science, (2009) 323:133-138.

(Continued)

*Primary Examiner* — Teresa E Strzelecka
(74) *Attorney, Agent, or Firm* — Robert H. Reamey

(57) ABSTRACT

The quality of information from single molecule analyses is improved by employing a method in which a single molecule reaction carried out within an optical confinement is monitored, the single molecule reaction is halted, and data from the optical confinement is obtained while the reaction is not occurring. Characteristic optical behavior observed while the reaction is halted is used to improve the quality of information obtained during the single molecule reaction, for example, by correcting the reaction data, excluding the reaction data, or providing a confidence level to the reaction data.

22 Claims, 11 Drawing Sheets

(56) References Cited

U.S. PATENT DOCUMENTS

| | | |
|---|---|---|
| 2004/0224319 A1 | 11/2004 | Sood et al. |
| 2004/0241716 A1 | 12/2004 | Kumar et al. |
| 2010/0221716 A1* | 9/2010 | Flusberg et al. ................ 435/6 |

OTHER PUBLICATIONS

Levene, M,J. et al., "Zero-Mode-Waveguides for Single-Molecule Analysis at High Concentrations" Science (2003) 299:682-686.

* cited by examiner

US 8,518,643 B2

METHOD TO IMPROVE SINGLE MOLECULE ANALYSES

CROSS-REFERENCE TO RELATED APPLICATIONS

This application claims the benefit of U.S. Provisional Application No. 61/301,505, filed Feb. 4, 2010, the disclosure of which is incorporated herein by reference in its entirety for all purposes.

STATEMENT REGARDING FEDERALLY SPONSORED RESEARCH

Not Applicable.

BACKGROUND OF THE INVENTION

The optical measurement of reactions occurring at the single molecule level provides the ability to probe molecular interactions and molecular mechanisms that are not readily accessible when measured on ensembles of molecules. In particular, observing a single polymerase enzyme while it sequentially adds nucleotides to a growing strand provides an extremely effective method for performing nucleic acid sequencing.

Optical confinements such as zero-mode waveguides provide for the observation of single molecules by producing a small optical observation volume, allowing for detection of signal from the reaction of a single molecule within the volume without the background signal which would be present in a larger observation volume. Substrates having thousands of optical confinements can be produced commercially to allow the monitoring of thousands of single molecules simultaneously.

Arrays of optical confinements having polymerase enzymes immobilized within them provide for the parallel sequencing of thousands of template nucleic acids at one time.

While arrays of optical confinements can be used for nucleic acid sequencing applications, the detection of single molecules provides an inherently small signal, which must be observed in the presence of background signals. There is a need for systems and methods that can more effectively identify and/or remove observed signals that do not correspond to a sequencing event in order to obtain higher quality sequencing information. The instant invention provides for such methods and systems.

BRIEF SUMMARY OF THE INVENTION

In some aspects, the invention provides an analytical method comprising: localizing a plurality of active molecules into optical confinements on a substrate whereby a plurality of the optical confinements comprise a single active molecule; exposing the single active molecules in the optical confinements to a reagent solution, whereby either the single active molecules or a reagent in the reagent solution or both comprise one or more fluorescent labels; initiating a reaction of the single active molecules; measuring fluorescence from the plurality of optical confinements over time to monitor the reaction and to obtain reaction data from each of the plurality of confinements; halting the reaction; measuring fluorescence from the plurality of optical confinements over time while the reaction is halted to obtain sticking data; and combining the sticking data with reaction data to provide a more accurate measurement of the reaction than if the sticking data was not used.

In some embodiments the sticking data is used to determine a set of optical confinements that are most likely to provide accurate information about the reaction. In some embodiments the active molecules comprise catalysts. In some embodiments the active molecules comprise enzymes. In some embodiments the enzymes comprise polymerases, reverse transcriptases, or ribosomes. In some embodiments pH, temperature, or light is used for halting of the reaction.

In some embodiments the addition of an active molecule deactivating compound is used for halting the reaction. In some embodiments an enzyme inhibitor is used for halting the reaction. In some embodiments the optical confinements comprise zero mode waveguides.

In some aspects, the invention provides a method of improving accuracy in single molecule sequencing comprising: localizing a plurality of polymerase enzyme complexes into optical confinements whereby a plurality of the optical confinements comprise a single active polymerase enzyme complex; exposing the polymerase enzyme complexes to a reagent solution comprising the components necessary for polymerase activity including a plurality of types of labeled nucleotides or nucleotide analogs, each type comprising a different label; initiating a sequencing reaction; measuring fluorescence from the plurality of optical confinements over time during the sequencing reaction to obtain sequencing data; halting the sequencing reaction; measuring fluorescence from the plurality of optical confinements over time while the sequencing reaction is halted to obtain sticking data; and using both the sticking data and the sequencing data to provide sequencing information that is more accurate than if the sticking data was not used.

In some embodiments the invention further comprises combining data from multiple optical confinements to produce combined sequencing data.

In some embodiments the sticking data is used to determine a set of optical confinements that are least likely to provide accurate information about the reaction, and eliminating the sequencing data from these optical confinements in the combined sequencing data.

In some embodiments the sticking data is used to determine a set of optical confinements that are most likely to provide accurate sequencing information and higher weight is given to the data from these optical confinements in producing the combined sequencing data.

In some embodiments the sequencing data and sticking data comprise data from four or more optical channels, each corresponding to a label on a type of nucleotide or nucleotide analog.

The method of claim 14 wherein the sticking data in one channel, two channels, three channels, or in four channels is used to improve the accuracy of sequencing information in that channel or set of channels.

In some embodiments the method further comprises, after halting the reaction to obtain sticking data, initiating the reaction again and measuring fluorescence from the plurality of optical confinements over time during the ensuing sequencing reaction to obtain subsequent sequencing data, and using the subsequent sequencing data along with the sticking data and the sequencing data to provide sequencing information.

In some embodiments each polymerase enzyme complex comprises a nucleic acid template. In some embodiments the nucleic acid template comprises DNA or RNA. In some embodiments the nucleic acid template is derived from genomic DNA, BACs, cDNA libraries, or PCR products.

In some embodiments halting the sequencing reaction comprises inhibiting the polymerase enzyme. In some embodiments the polymerase enzyme is inhibited by the addition of a polymerase enzyme inhibitor. In some embodiments the polymerase enzyme inhibitor comprises a reversible inhibitor. In some embodiments the polymerase enzyme inhibitor comprises an irreversible inhibitor. In some embodiments halting the sequencing reaction comprises denaturing or degrading the polymerase enzyme. In some embodiments halting the sequencing reaction comprises changing the pH, changing the temperature, irradiating the enzyme with electromagnetic radiation, or adding a chelating agent. In some embodiments halting the sequencing reaction comprises adding an inhibitor such that the reagent solution is diluted by less than 20%.

In some embodiments the optical confinements comprise zero-mode waveguides.

In some aspects, the invention provides an analysis instrument comprising: a substrate comprising optical confinements having a plurality of active molecules localized therein whereby a plurality of the optical confinements comprise a single active molecule; the substrate having a substrate reservoir which allows for exposing the single active molecules in the optical confinements to a reagent solution, whereby either the single active molecules or a reagent in the reagent solution or both comprise one or more fluorescent labels; an optical system for measuring fluorescence from the plurality of optical confinements over time to monitor the reaction and to obtain reaction data from each of the plurality of confinements and for measuring fluorescence from the plurality of optical confinements over time while the reaction is halted to obtain sticking data; a flow-cell in fluidic contact with the substrate for delivering agents to halt the reaction without moving the substrate; and a computer for combining the sticking data with reaction data.

In some embodiments the flow cell is in fluidic contact with an inhibitor reservoir comprising inhibitor in solution.

DETAILED DESCRIPTION OF THE INVENTION

General

Figure 1:
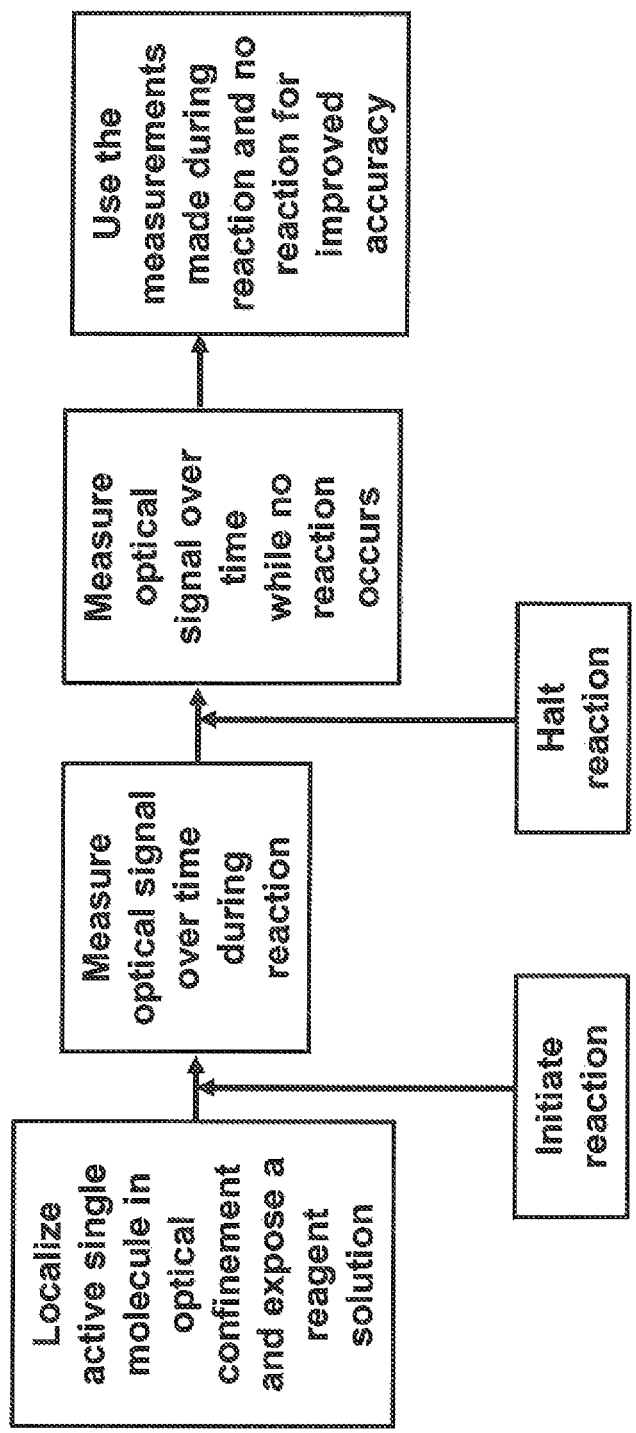
FIG. 1 shows a flow chart for an embodiment of a method of the invention.

The present invention relates to methods for improving the analysis of single-molecules within optical confinements. In some aspects, the invention involves monitoring single-molecule reactions of molecules of interest in a plurality of optical confinements, halting or inhibiting those reactions, monitoring the plurality of optical confinements while the single-molecule reaction is not occurring, and combining the information obtained when the reaction was not occurring with the information obtained when the reaction was occurring in order to improve the quality of the single-molecule analysis. The methods are particularly useful for the sequencing of nucleic acids using a polymerase enzyme. Optical confinements allow for monitoring small observation volumes, providing for monitoring the signal from a small number of labeled molecules, down to the level of single molecules. Optical confinements are described, for example, in U.S. patent application Ser. No. 7,292,742. The optical confinements of the invention include zero-mode waveguides (ZMWs), which can be produced by forming a nanometer scale hole in an opaque cladding layer that is disposed on a transparent substrate. ZMWs, generally being smaller than the diffraction dimensions of light that illuminates the ZMW through the transparent substrate, limit the penetration of light into the aperture of the ZMW, providing a small observation volume into which a molecule of interest can be disposed. The molecule of interest can comprise, for example, a catalyst molecule, such as an enzyme. The molecule of interest can comprise a binding entity such as an antibody or a receptor. The molecule of interest can also include a molecule or molecules that are associated with a catalyst or enzyme, such as an enzyme substrate. The molecule of interest may be labeled, or molecules dissolved in a solution in contact with the molecule of interest can be labeled.

One aspect of the invention allows for the observation of labeled analytes in solution which interact with a molecule of interest. A molecule of interest is immobilized within the observation volume of an optical confinement, and a solution comprising labeled analytes is contacted with the optical confinement. When a labeled analyte comes into contact with the molecule of interest, if it associates or binds with the molecule of interest, this interaction can be detected. Where there are differentially labeled analytes, it can be determined which of the analytes binds with the molecule of interest. The labeled molecules in solution can diffuse in and out of the observation volume rapidly, so while there will generally be some background signal from the labeled analytes, the characteristics of the signal from the rapidly diffusing labeled analytes can be distinguished from the signal of the labeled analytes that are bound or associated for a period of time with the molecule of interest. For example, pulse characteristics such as pulse duration or pulse shape can be used to distinguish the bound or associated species from the background. Other characteristics such as fluorescence lifetime, polarization, spectral shifts due to environment, FRET or combinations of these characteristics can be used to distinguish the bound or associated labeled analytes from the background.

Since the analysis can provide information about the interaction between single molecules, rather than information about an ensemble of molecules as is often the case for molecular analyses, unique information about the interaction of the molecule of interest and an analyte can be gathered. For example, where the interaction between the analyte and the molecule of interest constitutes a multi-step process, the individual steps can be seen at the single molecule level where such steps could be difficult or impossible to see by monitoring an ensemble of molecules. The observation of the actions of a single molecule can be useful for characterizing binding events or multi-step enzyme processes. Single molecule analysis can be particularly useful in performing sequencing by following the sequential addition of labeled units to a growing strand. Since each molecule of interest in an ensemble of molecules adds labeled units at a slightly different rate, the addition quickly goes out of sync between the various molecules of interest. In contrast, where the addition of labeled monomeric units such as labeled nucleotides are viewed at the single molecule level, there is no requirement for synchronization, providing the ability to perform sequencing at the rate of monomer addition.

Single molecule nucleic acid sequencing is described in more detail herein, and is described in Eid et al., Science, January, 2009, 133-138. For the method described in Eid et al., labeled nucleotides that associate directly with an immobilized polymerase enzyme can be identified as the nucleotides which become incorporated into the growing strand. Throughout this specification, the implementation of the invention may be described in the context of nucleic acid sequencing. It is to be understood that the methods of the invention can also be used for any other suitable non-sequencing analysis. Thus, where a system comprising a labeled nucleotide and a polymerase enzyme is described, the invention can apply equally to any suitable labeled analyte and suitable molecule of interest.

While analyses at the single-molecule level in optical confinements can have significant advantages, they can, in some cases, be affected by phenomena which are not significant for other types of analyses. The amount of signal that is generated by a single molecule is generally very low, and therefore small sources of optical noise, which may be of little or no consequence for other methods, can become significant sources of error. One such error source is referred to herein as "sticking". For example, there can be cases where a labeled nucleotide does not associate with a polymerase enzyme, but adheres non-specifically to a region near the polymerase enzyme for a relatively long period of time compared to diffusion through the observation volume. The signal that results from this non-specific adhesion can, in some cases, be mis-identified as a base incorporation, resulting in an error in sequence determination. This non-specific binding pulse can be referred to as a "stick". In addition to non-specific binding of labeled nucleotides or nucleotide analogs, sticking can be caused by other sources. For example, the optical system may detect other optical pulses which are mistakenly called as base incorporation due to noise within the system. Thus, pulses which have the characteristics of a pulse from an associated nucleotide or a nucleotide that is incorporated, but are not actually from the associated or incorporated nucleotide are sometimes referred to as "sticks".

We have performed measurements to understand the characteristics of sticks in the context of nucleic acid sequencing, and have found that sticks can have characteristics that are unlikely to be predicted. We have found that there are various characteristic types of sticking events. In many cases, we found that a specific optical confinement will show characteristic types of sticking events. For example, in some cases, where there are four labeled nucleotide analogs, the sticking in a particular optical confinement is seen in only one of the four optical channels. In other cases, sticking is seen in two, three, or all four of the channels. The timing and duration of the sticking events also varies, and a given optical confinement tends to show a particular characteristic timing and duration of sticks. For example, in some cases, the sticking occurs in bursts, and in some cases the sticking occurs as events spaced out over time.

Sticking can result in sequencing errors as the sticking pulses can mistakenly be called as incorporated nucleotides. While it is desirable to identify and eliminate sticking pulses, it can be difficult to do so with only the optical data obtained during a sequencing event, where it can be difficult to discern the difference between a sequencing pulse and a sticking pulse. Thus, where a number of optical confinements are simultaneously observed, some optical confinements will have low levels of sticking, yielding high quality information, while some optical confinements will have high levels of sticking, yielding lower quality information; and it can be difficult to discern the difference. In some types of sequencing analysis, the data from a number of different optical confinements is combined. For example, a sample may have multiple copies of a region of a sequence, and each of the copies end up in a different optical confinement where they are sequenced. After sequencing in the individual optical confinements, the data from multiple optical confinements is often combined. Where data from an optical confinement that is of poorer quality is combined with higher quality data from other optical confinements, the quality of the combined data can suffer.

One aspect of the invention involves measuring the sticking characteristics of a plurality of optical confinements on a chip while a sequencing reaction is not occurring, and using these measurements to improve the accuracy of the data obtained when the sequencing reaction is running. This approach is particularly useful because, as described above, a given optical confinement will tend to have characteristic stickiness characteristics. In some cases, the stickiness characteristics of an optical confinement can be used to correct the sequencing data from that optical confinement, for example providing a filter that can be used to correct one or more channels of data that show stickiness.

Knowing the characteristics of the background stickiness of the optical confinement allows for more effective algorithms for deciding whether a given pulse is an incorporation event or not. For example, if it is known that the stickiness of a particular optical confinement involves a series of bursts of a given duration in the red channel, then the data from the red channel can be analyzed to identify and remove such bursts from the sequencing data, thereby improving accuracy. In other cases, the stickiness data can be used to eliminate data from a given optical confinement, or to eliminate the data from a given optical channel in an optical confinement, in order to prevent the data from lowering the accuracy from other optical confinements. The stickiness data can be used to provide a weight to the data from a given optical confinement as it is combined with other data. For example, instead of eliminating the data, the data can be included but provided a lower weight, such that other conflicting data can be allowed to override the data from this channel where there is a conflict.

For the methods of the invention, the stickiness data, obtained when no reaction is occurring, is generally obtained under the same conditions as those for which sequencing occurs. The conditions that held the same for measuring sequencing data and stickiness data include, for example, having the same enzyme, template, and primer of a polymerase enzyme complex. In addition, the relative concentrations of most of the sequencing reagents should be the same. In particular, the concentration of the labeled nucleotides or nucleotide analogs should generally be the same or similar when measuring stickiness and when measuring sequencing. For example, the concentration of labeled nucleotides should be within about 1 percent, about 5 percent, about 10 percent, about 15 percent, about 25 percent, or about 30% of the concentration of labeled nucleotides during sequencing. The concentration of labeled nucleotides during sequencing can be the concentration of labeled nucleotides at the beginning of the sequencing reaction, the concentration of labeled nucleotides at the completion of the sequencing reaction, or an intermediate value such as the average or median concentration of nucleotides during the sequencing reaction. In general, the temperature, pH, and humidity are maintained at substantially the same level while measuring stickiness and measuring sequencing unless these are used, as described below to inhibit the activity of the enzyme. It will be understood by those of skill in the art that different types of reactions will have different sensitivity to reaction conditions. For example, some reactions will be very sensitive to changes in pH, while others will show little pH sensitivity. The sensitivity of a given reaction of interest to the various reaction conditions can be readily determined by monitoring the reactions under the different conditions.

In some cases, the stickiness data is obtained prior to the sequencing reaction. This approach can be useful, as the stickiness data is available prior to obtaining any sequencing data, and thus could be used to process the sequencing data as it is being obtained, or for example, for making a decision not to monitor the sequencing in certain optical confinements. Where fluorescence detection is used, one issue with this approach is that in order to obtain the stickiness data, the polymerase and sequencing reagents are exposed to illumination light for the time in which the stickiness data is obtained. In some cases, photodamage can be a factor in limiting the read length in a sequencing reaction, and therefore the exposure of the reaction to illumination light prior to carrying out sequencing can increase the likelihood of photodamage. Thus, where measurement of stickiness before sequencing is used, it can be desirable to measure stickiness over relatively short periods of time in order to minimize photodamage. For example, in some cases the measurements are taken over a period of 5 sec to about 10 minutes. In some cases the measurements are taken from about 30 seconds to about 3 minutes. In some cases the measurements are taken for about 30 seconds, about 1 minute, about 3 minutes, or about 7 minutes. In some embodiments, stickiness can be measured prior to attaching a the active single molecule in the optical confinement.

Measuring stickiness after the sequencing reaction is complete allows for determining stickiness within each optical confinement without compromising read length due to photodamage. In one aspect of the invention, the sequencing reaction is halted, and the reaction is monitored while no sequencing is occurring in order to measure stickiness. The reaction can be halted, for example, by inhibiting the polymerase enzyme by adding an enzyme inhibitor. In some cases, the enzyme inhibitor can be added to the reaction without substantially affecting other aspects of the reaction such as the concentration of the sequencing reagents such as the labeled nucleotides.

Suitable inhibitors include antibiotics, drugs, chelating agents, product inhibitors, binding proteins, and electromagnetic radiation such as UV or visible light.

One aspect of the invention comprises an array of optical confinements on a substrate wherein the substrate comprises a substrate reservoir for containing the reagent solution during the reaction. In some embodiments, the substrate reservoir is fluidically connected via a flow cell to an inhibitor reservoir for delivering an inhibitor for the polymerase reaction. In some embodiments the flow cell is connected to a reservoir for delivering inhibitor and a reversal reagent reservoir for delivering an inhibitor reversal reagent. In some cases, the flow cell has an outlet to allow for the removal of liquid from the array of optical confinements. The flow cell allows for introducing reagents for halting, and/or for re-starting the single molecule reaction without having to remove the substrate having the optical confinements during the process. For example, the flow cell is mounted in a portion of an instrument having excitation and illumination optics such that the optical confinements are properly aligned with the optical system. Using the flow cell, the reaction can be initiated, halted, and re-initiated by moving fluid to and/or from the substrate without adversely affecting the alignment of the optics.

In some cases, sequencing can be carried out both before and after the period of time during which stickiness is measured, or carried out at during a time period in the middle of the reaction. This can be done, for example, using a reversible inhibitor.

The paragraphs above describe embodiments of the invention in the context of nucleic acid sequencing. As mentioned above, the methods of the invention are suitable for single-molecule analyses which do not involve nucleic acid sequencing. For example, the single molecule analysis could involve measuring the association between a receptor and one or more analytes, or measuring the activity of an enzyme such as a phosphatase, kinase, esterase, peptidase, nuclease, lyase or hydrolase. The methods of the invention could also be used for the observation of protein synthesis with single ribosomes as described in copending U.S. Provisional Patent Application 61/186,645 filed Jun. 12, 2009 which is incorporated by reference herein for all purposes. For these systems, single molecule analyses can be performed in which one or more labeled analytes are in solution in contact with the enzyme or receptor which is immobilized in an optical confinement. The interaction between the labeled analyte and the enzyme or receptor is measured by the characteristic signals obtained when the analyte is associated with or bound to the enzyme or receptor. As with sequencing, these systems can have signals in their optical confinements that have similar characteristics to a bound or associated labeled analyte, but do not represent actual binding events. The methods of the invention can be used in these systems to improve the accuracy of the analysis by measuring the signal from the optical confinements when a binding or association event cannot occur, and use this measurement in order to improve the accuracy of information obtained during the binding or association reaction.

FIG. 1 shows a flow chart of an embodiment of a method of the invention. An active single molecule such as an enzyme, receptor, binding agent, or catalyst is localized within an optical confinement. The optical confinement can be a ZMW, and the method is generally carried out using a substrate having multiple optical confinements. The number of optical confinements can be from about 10 to about a million or more. The localization can include immobilization of the active single molecule within the optical confinement. The active single molecule can be bound directly or through a linker group to the surface, or the active molecule can be bound indirectly by associating with another molecule, such as a substrate for an enzyme that is bound to the surface. It is generally desirable for a portion of the optical confinements on the substrate to have only one active single molecule localized within it. Methods of localizing an active single molecule within an optical confinement are described, for example in U.S. patent application Ser. No. 12/384,097 filed Mar. 30, 2009. The localized active single molecule is then exposed to the reagents needed for carrying out the reaction which is being analyzed, for example the binding reaction, the enzymatic reaction, the catalytic reaction, the polymerase reaction, etc. In some embodiments of the invention, the reagent solution will comprise labeled analyte molecules. In some cases, multiple analyte molecules, each with different labels are present in the reagent solution.

The reaction is then initiated. In some cases, the addition of the reagent solution itself will constitute initiation. In other cases, a separate initiation step will be carried out. Enzymatic reactions can often be initiated by the addition of an essential component as a separate step. For example, a DNA polymerase can be initiated by adding a divalent metal such as Manganese or Magnesium. Once the reaction is initiated, the optical signal from the optical confinements is measured over time. These measurements provide the information for analyzing the interaction between the labeled analyte and the active single molecules. The reaction is then halted. In some cases, the reaction will stop on its own without intervention. In other cases, a reagent or change of conditions is used in order to halt the reaction. The optical signal is measured over time while no reaction is occurring in the optical confinements. These measurements can be referred to as sticking measurements and the data obtained from them as sticking data. It is generally preferred that the conditions during the reaction and while the reaction is halted are as similar as possible so that the measurements during while no reaction is occurring is as comparable as possible to the measurements when the reaction is occurring. In particular, it is desirable that the concentration of labeled components such as labeled analyte be similar for both sets of measurements.

Figure 2:
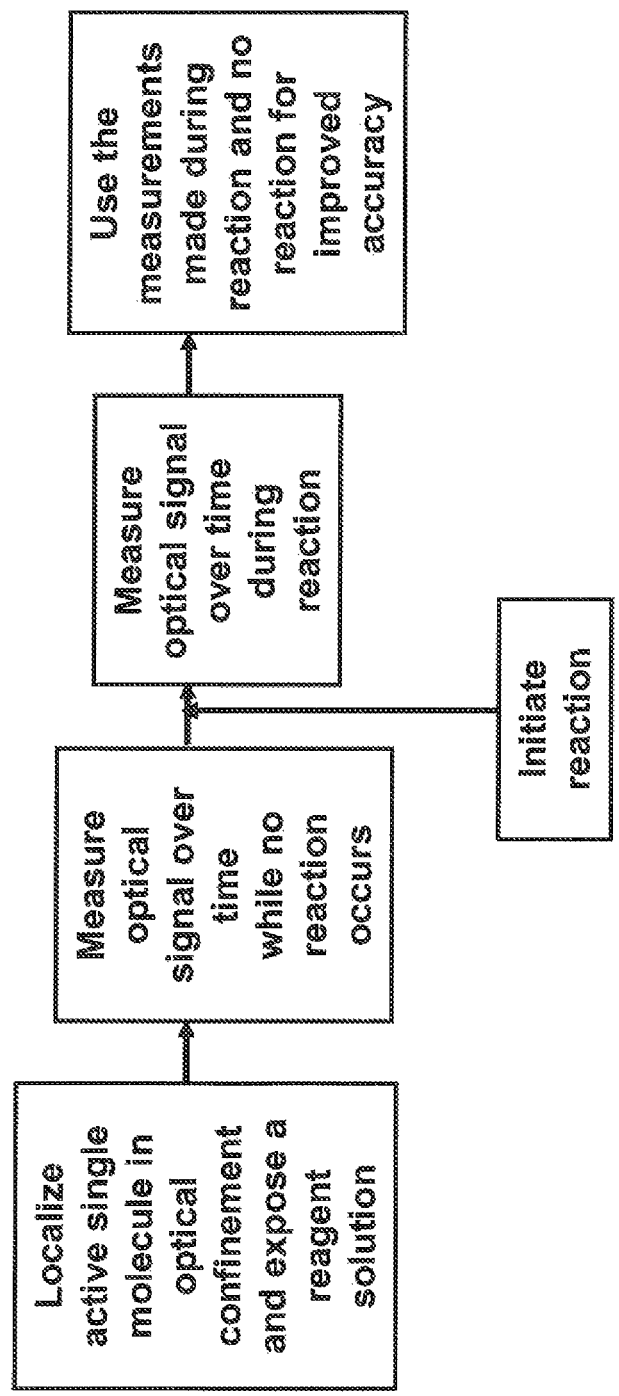
FIG. 2 shows a flow chart for another embodiment of a method of the invention.

FIG. 2 shows a flow chart illustrating another embodiment of the invention. Here, the active single molecule in an optical confinement is exposed to a reagent solution. In some cases the active single molecule is a polymerase enzyme, and the reagent solution provides the elements required for template directed, polymerase mediated nucleic acid synthesis including labeled nucleotide analogs. Prior to initiation, the optical signal over time is observed from the optical confinement. The single molecule reaction is then initiated, and the signal over time is measured while the single molecule reaction is occurring.

The measurements made when no reaction occur provide information about each specific optical confinement which can be used to improve the accuracy of the information obtained during the reaction. As described above, the sticking information can be used to improve, eliminate, or to weigh the information obtained in a particular optical confinement.

Thus, the invention in some aspects provides an analytical method comprising: localizing a plurality of active molecules into optical confinements on a substrate whereby a plurality of the optical confinements comprise a single active molecule; exposing the single active molecules in the optical confinements to a reagent solution, whereby either the single active molecules or a reagent in the reagent solution or both comprise one or more fluorescent labels; initiating a reaction of the single active molecules; measuring fluorescence from the plurality of optical confinements over time to monitor the reaction and to obtain reaction data from each of the plurality of confinements; halting the reaction; measuring fluorescence from the plurality of optical confinements over time while the reaction is halted to obtain sticking data; and combining the sticking data with reaction data to provide a more accurate measurement of the reaction than if the sticking data was not used.

Optical Confinements—Zero-mode Waveguides

In some embodiments of the methods and systems of the invention, optical confinements are used to enhance the ability to concurrently observe multiple single active molecules such as single polymerase enzyme complexes simultaneously. In general, optical confinements are disposed upon a substrate and used to provide electromagnetic radiation to or derive such radiation from only very small spaces or volumes. Such optical confinements may comprise structural confinements, e.g., wells, recesses, conduits, or the like, or they may comprise optical processes in conjunction with other components, to provide illumination to or derive emitted radiation from only very small volumes. Examples of such optical confinements include systems that utilize, e.g., total internal reflection (TIR) based optical systems whereby light is directed through a transparent portion of the substrate at an angle that yields total internal reflection within the substrate.

The substrates of the invention are generally rigid, and often planar, but need not be either. Where the substrate comprises an array of optical confinements, the substrate will generally be of a size and shape that can interface with optical instrumentation to allow for the illumination and for the measurement of light from the optical confinements. Typically, the substrate will also be configured to be held in contact with liquid media, for instance containing reagents and substrates and/or labeled components for optical measurements.

Where the substrates comprise arrays of optical confinements, the arrays may comprise a single row or a plurality of rows of optical confinement on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is sometimes preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

In accordance with the invention, arrays of confinements, e.g., zero mode waveguides, are provided in arrays of more than 100, more than 1000, more than 10,000, more that 100,000, or more than 1,000,000 separate waveguides on a single substrate. In addition, the waveguide arrays typically comprise a relatively high density of waveguides on the surface of the substrate. Such high density typically includes waveguides present at a density of greater than 10 zero mode waveguides per $mm^2$, preferably, greater than 100 waveguides per $mm^2$ of substrate surface area, and more preferably, greater than 500 or even 1000 waveguides per $mm^2$ and in many cases up to or greater than 100,000 waveguides per $mm^2$. Although in many cases, the waveguides in the array are spaced in a regular pattern, e.g., in 2, 5, 10, 25, 50 or 100 or more rows and/or columns of regularly spaced waveguides in a given array, in certain preferred cases, there are advantages to providing the organization of waveguides in an array deviating from a standard row and/or column format. In preferred aspects, the substrates include zero mode waveguides as the optical confinements to define the discrete reaction regions on the substrate.

The overall size of the array of optical confinements can generally range from a few nanometers to a few millimeters in thickness, and from a few millimeters to 50 centimeters in width and/or length. Arrays may have an overall size of about few hundred microns to a few millimeters in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements may be placed close to each other relative to the incident wavelength.

The optical confinements can be zero-mode-waveguides. Zero mode waveguides have been described in, e.g., U.S. Pat. No. 6,917,726, the full disclosure of which is incorporated herein by reference in its entirety for all purposes. Generally, such waveguides comprise a core disposed through a cladding layer, which in the case of applications to reactions, comprises an aperture disposed through the cladding layer that can receive the reactants to be monitored. Typically, the aperture has at least one cross-sectional dimension, e.g., diameter, which is sufficiently small that light entering the waveguide is prevented in some measure from propagating through the core, effectively resulting in a very small portion of the core and its contents being illuminated, and/or emitting optical signals that exit the core. In the case of optical signals (and excitation radiation), the waveguide cores will typically be between about 1 nm and about 300 nm, between about 10 and about 200 nm, or between about 50 and about 150 nm in diameter where light in the visible range is used.

The individual confinement in the array can provide an effective observation volume less than about 1000 zeptoliters, less than about 900, less than about 200, less than about 80, less than about 10 zeptoliters. Where desired, an effective observation volume less than 1 zeptoliter can be provided. In a preferred aspect, the individual confinement yields an effective observation volume that permits resolution of individual molecules, such as enzymes, present at or near a physiologically relevant concentration. The physiologically relevant concentrations for many biochemical reactions range from micro-molar to millimolar because most of the enzymes have their Michaelis constants in these ranges. Accordingly, preferred array of optical confinements has an effective observation volume for detecting individual molecules present at a concentration higher than about 1 micromolar ($\mu$M), or more preferably higher than 50 $\mu$M, or even higher than 100 $\mu$M.

The optical confinements of the inventions generally comprise structures which are smaller than the wavelength of light that interacts with them. The optical confinements generally concentrate or exclude light so as to produce an observation volume which can be significantly smaller than the dimensions of the wavelength of the light. Preferred optical confinements comprise zero-mode waveguide (ZMW) structures. The optical confinements also include arrays of such ZMWs, and systems incorporating them. ZMW structures can be used to analyze solutions containing luminescent species disposed inside or in close proximity to the ZMW.

Figure 3:
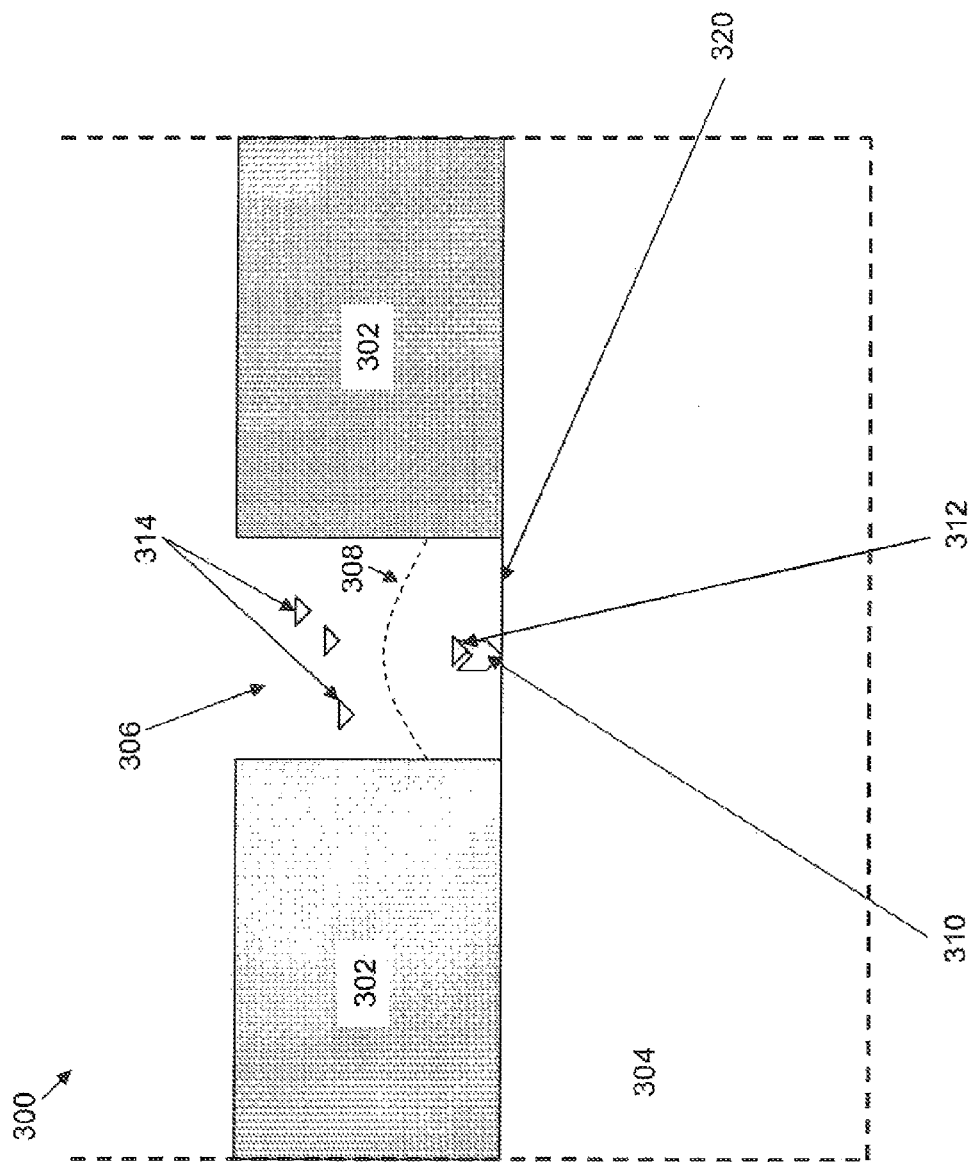
FIG. 3 is a drawing illustrating how a zero mode waveguide provides for the illumination of a small volume having an active single molecule immobilized within it.

The basic structure of a ZMW is schematically illustrated in FIG. 3. As shown, a ZMW structure 300 is provided that includes a cladding layer 302 deposited upon a transparent layer 304. An aperture or core 306 is disposed through the cladding layer to expose the transparent layer 304 below. The aperture 306 has a base 320 that comprises the top surface of the transparent layer 304. As shown in FIG. 3, the base 320 of the aperture 306 is at the same level as the planar surface of the transparent layer 304. In some cases, the base 320 of the aperture 306 is not at the same level, and can be above or below the planar surface of the transparent layer 304 outside of the aperture. For example, in some cases, the base of the aperture can be below the level of the surface of the transparent 304, extending into the transparent layer 304.

The core is dimensioned to provide optical confinement by attenuating or preventing propagation of electromagnetic radiation that falls below a cut-off frequency through the core. Instead, the light only penetrates a short distance into the core, illuminating a relatively small volume, indicated as bounded by the dashed line 308. By providing reactants of interest within the observation volume, e.g., enzyme 310 and analyte 312, one can selectively observe their operation without interference from reactants, e.g., analytes 314 outside the observation volume, e.g., above line 308. It will be understood by those in the art the intensity will fall off in the core with a certain function, e.g. exponentially, and that line 308 does not necessarily represent a line above which no light penetrates, but can represent, for example, a line at which the light falls to a certain absolute or relative intensity level.

ZMW structures can be used in order to observe very small quantities of analytes, and have been shown to provide information on the presence and behavior of an analyte to the level of a single molecule. The ability to observe a single molecule in real time allows for carrying out single molecule sequencing, for example single molecule nucleic acid sequencing.

As zero-mode-waveguide can provide an optical guide in which the majority of incident radiation is attenuated, preferably more than 80%, more preferably more than 90%, even more preferably more than 99% of the incident radiation is attenuated. As such high level of attenuation, no significant propagating modes of electromagnetic radiation exist in the guide. Consequently, the rapid decay of incident electromagnetic radiation at the entrance of such guide provides an extremely small observation volume effective to detect single-molecules, even when they are present at a concentration as high as in the micromolar range.

The zero-mode-waveguide of the present invention typically comprises a cladding surrounding a core (i.e., partially or fully), wherein the cladding is configured to preclude propagation of electromagnetic energy of a wavelength higher than the cutoff wavelength longitudinally through the core of the zero-mode waveguide. The cladding is typically made of materials that prevent any significant penetration of the electric and the magnetic fields of an electromagnetic radiation that is opaque and/or reflective materials. Suitable materials for fabricating the cladding include but are not limited to metals, metal oxides, alloys, and semi-conducting materials, and any combination thereof.

The internal cavity (i.e., the core) surrounded by the cladding may adopt a convenient size, shape or volume so long as propagating modes of electromagnetic radiation in the guide is effectively prevented. The core typically has a lateral dimension less than the cutoff wavelength ($\lambda c$). For a circular guide of diameter d and having a clad of perfect conductor, $\lambda c$ is approximately 1.7 times d. The cross sectional area of the core may be circular, elliptical, oval, conical, rectangular, triangular, polyhedral, or in any other shape. Although uniform cross sectional area is generally preferred, the cross sectional area may vary at any given depth of the guide if desired.

The optical performance of the ZMW can be enhanced by incorporation within a micromirror structure on the substrate. The incorporation of micromirrors and other methods of improving optical performance in multiplex systems are describe in copending U.S. patent application Ser. No. 12/567,526, filed Sep. 25, 2009.

In the context of chemical or biochemical analyses within ZMWs as well as other optical confinements, it is generally desirable to ensure that the reactions of interest are taking place within the optically interrogated portions of the confinement, at a minimum, and preferably such that only the reactions of a single molecule is occurring within an interrogated portion of an individual confinement. A number of methods may generally be used to provide individual molecules within the observation volume. A variety of these are described in co-pending U.S. patent application Ser. No. 11/240,662, filed Sep. 30, 2005, incorporated herein by reference in its entirety for all purposes, which describes, inter alia, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these.

Single Molecule Sequencing

In the context of single molecule nucleic acid sequencing analyses, a single immobilized nucleic acid synthesis complex, comprising a polymerase enzyme, a template nucleic acid, whose sequence one is attempting to elucidate, and a primer sequence that is complementary to a portion of the template sequence, is observed to identify individual nucleotides as they are incorporated into the extended primer sequence. Incorporation is typically monitored by observing an optically detectable label on the nucleotide, prior to, during or following its incorporation. In some cases, such single molecule analyses employ a "one base at a time approach", whereby a single type of labeled nucleotide is introduced to and contacted with the complex at a time. Upon incorporation, unincorporated nucleotides are washed away from the complex, and the labeled incorporated nucleotides are detected as a part of the immobilized complex.

In some instances, only a single type of nucleotide is added to detect incorporation. These methods then require a cycling through of the various different types of nucleotides (e.g., A, T, G and C) to be able to determine the sequence of the template. Because only a single type of nucleotide is contacted with the complex at any given time, any incorporation event is by definition, an incorporation of the contacted nucleotide. These methods, while somewhat effective, generally suffer from difficulties when the template sequence includes multiple repeated nucleotides, as multiple bases may be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but are distinguishable by the presence on each type of nucleotide of a different optical label. Accordingly, such methods can use a single step to identify a given base in the sequence. In particular, all four nucleotides, each bearing a distinguishable label, is added to the immobilized complex. The complex is then interrogated to identify which type of base was incorporated, and as such, the next base in the template sequence.

In some cases, these methods only monitor the addition of one base at a time, and as such, they (and in some eases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

In another process, single molecule primer extension reactions are monitored in real-time, to identify the continued incorporation of nucleotides in the extension product to elucidate the underlying template sequence. In such single molecule real time (or SMRT™) sequencing, the process of incorporation of nucleotides in a polymerase mediated template dependent primer extension reaction is monitored as it occurs. In preferred aspects, the template/polymerase primer complex is provided, typically immobilized, within an optically confined region, such as a zero mode waveguide, or proximal to the surface of a transparent substrate, optical waveguide, or the like (see e.g., U.S. Pat. Nos. 6,917,726, and 7,170,050 and Published U.S. Patent Application No. 2007-0134128, the full disclosures of which are hereby incorporated herein by reference in their entirety for all purposes).

The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated.

Figure 4:
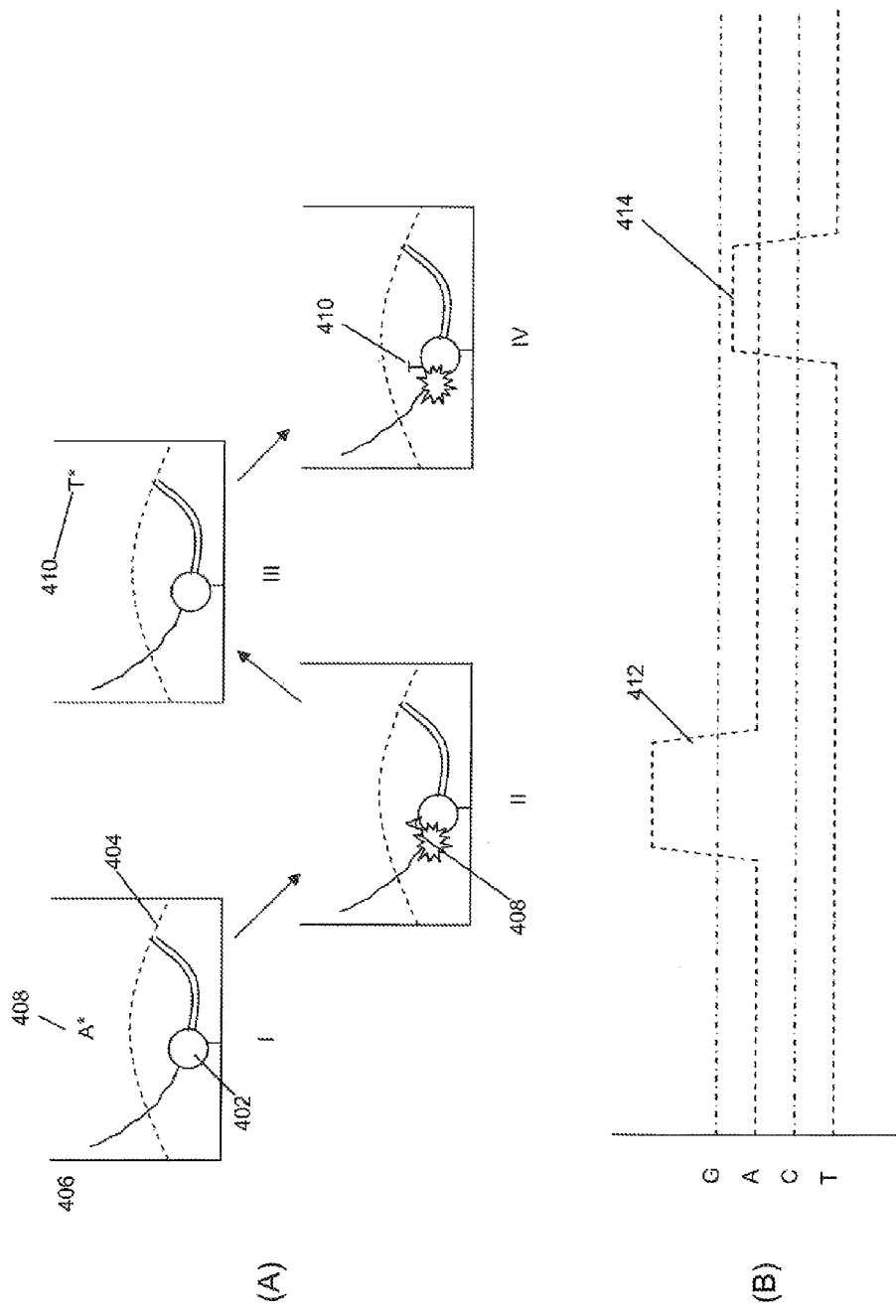
FIG. 4 is a schematic illustration of how single molecule sequencing can be carried out in an optical confinement.

A schematic illustration of this sequencing process is shown in FIG. 4. As shown in FIG. 4A, an immobilized complex 402 of a polymerase enzyme, a template nucleic acid and a primer sequence are provided within an observation volume (as shown by dashed line 404) of an optical confinement, of e.g., a zero mode waveguide 406. As an appropriate nucleotide analog, e.g., nucleotide 408, is incorporated into the nascent nucleic acid strand, it is illuminated for an extended period of time corresponding to the retention time of the labeled nucleotide analog within the observation volume during incorporation which produces a signal associated with that retention, e.g., signal pulse 412 as shown by the A trace in FIG. 4B. Once incorporated, the label that attached to the polyphosphate component of the labeled nucleotide analog, is released. When the next appropriate nucleotide analog, e.g., nucleotide 410, is contacted with the complex, it too is incorporated, giving rise to a corresponding signal 414 in the T trace of FIG. 4B. By monitoring the incorporation of bases into the nascent strand, as dictated by the underlying complementarity of the template sequence, one can obtain long stretches of sequence information of the template. Further, in order to obtain the volumes of sequence information that may be desired for the widespread application of genetic sequencing, e.g., in research and diagnostics, higher throughput systems are desired.

By way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments. In preferred aspects, the various different complexes are provided arrayed upon a substrate. Such arrayed complexes may be provided within optically or structurally confined structures, e.g., zero mode waveguides, or they may be patterned on a surface. Alternatively, they may be randomly disposed over a surface but subjected to targeted arrayed illumination, or detection, such that only complexes within an array pattern on the surface are monitored. For purposes of discussion herein, both configurations are referred to herein as the monitoring of arrayed complexes, or the like.

Polymerase Enzymes

Polymerase enzymes having labels indicative of polymer conformation can include polymerases mutated to have desirable properties for sequencing. For example, suitable enzymes include those taught in, e.g., WO 2007/076057 POLYMERASES FOR NUCLEOTIDE ANALOGUE INCORPORATION by Hanzel et al., WO 2008/051530 POLYMERASE ENZYMES AND REAGENTS FOR ENHANCED NUCLEIC ACID SEQUENCING by Rank et al., and U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES." The modified polymerases may have modified properties such as (e.g., decreased branch fraction formation, improved specificity, improved processivity, altered rates, improved retention time, improved stability of the closed complex, etc.).

In addition, the polymerases can be further modified for application-specific reasons, such as to increase photostability, e.g., as taught in U.S. patent application Ser. No. 12/384, 110 filed Mar. 30, 2009, by Keith Bjornson et al. entitled "Enzymes Resistant to Photodamage," to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

DNA Polymerases

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include PhusionrM High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287.

In some cases, the active single molecule can comprise a fusion protein between the polymerase and another functional protein to modify enzyme performance. The fusion protein can be, for example, a polymerase enzyme fused to a single stranded binding protein.

RNA Polymerases

In some embodiments, the polymerase enzyme that is used for sequencing is an RNA polymerase. Any suitable RNA polymerase can be used including RNA polymerases from bacteria, eukaryotes, viruses, or archea. Suitable RNA polymerases include RNA Pol I, RNA Pol II, RNA Pol III, RNA Pol IV, RNA Pol V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from *E. coli* and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e. they help RNAP choose whether or not to express certain genes. RNA dependent RNA polymerases (RNA replicases) may also be used including viral RNA polymerases: e.g. poliovirus 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or systems of the invention include RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Reaction Conditions

The reaction conditions can be adjusted to allow the reaction of the active molecule of interest to proceed. The specific conditions will depend on the active molecule which is used. In some cases, the molecule of interest or conditions can be adjusted to control the rate of the reaction. Recombinant polymerases of the invention are optionally modified in a manner in which the relative rates of steps of the polymerization reaction are changed, for example, such that the polymerase is capable of showing two slow-step characteristics. Reaction conditions can be manipulated, for example, to further slow a step or steps which are already slowed in a modified polymerase, or to slow an additional step, such that the resulting polymerase system exhibits two slow step behavior.

The polymerase reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors. Manipulation of reaction conditions to achieve or enhance two slow step behavior of polymerases is described in detail in U.S. patent application Ser. No. 12/414,191 filed Mar. 30, 2009, and entitled "Two slow-step polymerase enzyme systems and methods."

Enzymatic reactions are often run in the presence of a buffer, which is used, in part, to control the pH of the reaction mixture. The type of buffer can in some cases influence the kinetics of the polymerase reaction in a way that can lead to two slow-step kinetics. For example, in some cases, use of TRIS as buffer is useful for obtaining a two slow-step reaction. Suitable buffers include, for example, TAPS (3-{[tris (hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl) methylglycine), HEPES 4-2-hydroxyethyl-1-piperazineethanesulfonic acid), TES (2-{[tris (hydroxymethyl)methyl]amino}ethanesulfonic acid), MOPS (3-(N-morpholino)propanesulfonic acid), PIPES (piperazine-N,M-bis(2-ethanesulfonic acid)), and MES (2-(N-morpholino)ethanesulfonic acid).

The pH of the reaction can influence the kinetics of the polymerase reaction. The pH can be adjusted to a value that produces a two slow-step reaction mechanism. The pH is generally between about 6 and about 9. In some cases, the pH is between about 6.5 and about 8.0. In some cases, the pH is between about 6.5 and 7.5. In some cases, the pH is about 6.5, 6.6, 6.7, 6.8, 6.9, 7.0, 7.1, 7.2, 7.3, 7.4, or 7.5.

The temperature of the reaction can be adjusted. The reaction temperature may depend upon the type of polymerase which is employed. Temperatures between 15° C. and 90° C., between 20° C. and 50° C., between 20° C. and 40° C., or between 20° C. and 30° C. can be used.

In some cases, additives can be added to the reaction mixture that will influence the kinetics of the polymerase reaction. In some cases, the additives can interact with the active site of the enzyme, acting for example as competitive inhibitors. In some cases, additives can interact with portions of the enzyme away from the active site in a manner that will influence the kinetics of the reaction so as to produce a reaction exhibiting two slow steps. Additives that can influence the kinetics include, for example, competitive but otherwise unreactive substrates or inhibitors in analytical reactions to modulate the rate of reaction as described in copending U.S. Utility patent application Ser. No. 12/370,472, the full disclosure of which is incorporated herein by reference in its entirety for all purposes.

As another example, an isotope such as deuterium can be added to influence the rate of one or more step in the polymerase reaction. In some cases, deuterium can be used to slow one or more steps in the polymerase reaction due to the deuterium isotope effect. By altering the kinetics of steps of the polymerase reaction, in some instances two slow step kinetics, as described herein, can be achieved. The deuterium isotope effect can be used, for example, to, control the rate of incorporation of nucleotide, e.g., by slowing the incorporation rate. Isotopes other than deuterium can also be employed, for example, isotopes of carbon (e.g. $^{13}C$), nitrogen, oxygen, sulfur, or phosphorous.

As yet another example, additives that can be used to control the kinetics of the polymerase reaction include the addition of organic solvents. The solvent additives are generally water soluble organic solvents. The solvents need not be soluble at all concentrations, but are generally soluble at the amounts used to control the kinetics of the polymerase reaction. While not being bound by theory, it is believed that the solvents can influence the three dimensional conformation of the polymerase enzyme which can affect the rates of the various steps in the polymerase reaction. For example, the solvents can affect steps involving conformational changes such as the isomerization steps. Added solvents can also affect, and in some cases slow, the translocation step. In some cases, the solvents act by influencing hydrogen bonding interactions.

The water miscible organic solvents that can be used to control the rates of one or more steps of the polymerase reaction in single molecule sequencing include, e.g., alcohols, amines, amides, nitriles, sulfoxides, ethers, and esters and small molecules having more than one of these functional groups. Exemplary solvents include alcohols such as methanol, ethanol, propanol, isopropanol, glycerol, and small alcohols. The alcohols can have one, two, three, or more alcohol groups. Exemplary solvents also include small molecule ethers such as tetrahydrofuran (THF) and dioxane, dimethylacetamide (DMA), dimethylsulfoxide (DMSO), dimethylformamide (DMF), FMP, TMP, and acetonitrile.

The water miscible organic solvent can be present in any amount sufficient to control the kinetics of the polymerase reaction. The solvents are generally added in an amount less than 40% of the solvent weight by weight or volume by volume. In some embodiments the solvents are added between about 0.1% and 30%, between about 1% and about 20%, between about 2% and about 15%, and between about 5% and 12%. The effective amount for controlling the kinetics can be determined by the methods described herein and those known in the art.

One aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interaction in polymerase reactions, see, e.g., Arndt, et al., Biochemistry (2001) 40:5368-5375. Suitable conditions include those described in U.S. patent application Ser. No. 12/384,112 filed Mar. 30, 2009.

Template Nucleic Acids

The template nucleic acids of the invention can comprise any suitable polynucleotide, including double-stranded DNA, single-stranded DNA, single-stranded DNA hairpins, DNA/RNA hybrids, RNAs with a recognition site for binding of the polymerizing agent, and RNA hairpins. Further, target polynucleotides may be a specific portion of a genome of a cell, such as an intron, regulatory region, allele, variant or mutation; the whole genome; or any portion thereof. In other embodiments, the target polynucleotides may be mRNA, tRNA, rRNA, ribozymes, antisense RNA or RNAi. The target polynucleotide may be of any length, such as at between about 10 bases and about 100,000 bases, or between about 100 bases and 10,000 bases.

The target nucleic acids can be prepared prior to being sequenced, for example fragmented to appropriate size ranges, capped, tagged, or ligated to specific sequences, such as universal priming sites. The target nucleic acids can be circular or linear. Suitable templates are described, for example in U.S. patent application Ser. No. 12/413,258 entitled "Compositions and Methods for Nucleic Acid Sequencing."

The template nucleic acids of the invention can include unnatural nucleic acids such as PNAs, modified oligonucleotides (e.g., oligonucleotides comprising nucleotides that are not typical to biological RNA or DNA, such as 2'-O-methylated oligonucleotides), modified phosphate backbones and the like. A nucleic acid can be e.g., single-stranded or double-stranded.

Localizing or Immobilizing

The molecules of interest for single molecule analysis can be immobilized within optical confinement such as the zero-mode waveguide by any suitable means, many of which are well known in the art. The methods of the invention can include a silica-based or transparent layer that is functionalized. This functionalization is carried out using a functionalizing agent or coupling agent which reacts with the silica-based or transparent surface. As used herein, a coupling agent is generally a compound that binds to the surface, and also comprises a coupling group that can react with another compound, for example, to bind a molecule of interest such as an enzyme to the surface. A functionalizing agent is a compound that binds to the silica-based or transparent surface that does not necessarily have a separate coupling group for subsequent binding of another compound. The functionalizing agent will generally provide a characteristic or functionality to the silica or transparent region. Such characteristic or functionality could be a chemical or physical characteristic. For example, the functionalizing agent could comprise optically detectable agents that are sensitive to the medium into which the surface is disposed. The terms coupling agent and functionalizing agent are not mutually exclusive. In some cases a functionalizing agent could comprise a reactive group and thus could be used as a coupling agent.

Coupling of functional groups to the surface may be carried out by any of a variety of methods known in the art. For example, in the context of silica based substrates, e.g., glass, quartz, fused silica, silicon, or the like, well characterized silane chemistries may be used to couple other groups to the surface. Such other groups may include functional groups, activatable groups, and/or linker molecules to either of the foregoing, or the actual molecules of interest that are intended for use in the end application of the surface. In the context of other transparent material types, e.g., polymeric materials, or the like, other processes may be employed, e.g., using hybrid polymer surfaces having functional groups coupled thereto or extending from the polymer surface using, e.g., copolymers with functional groups coupled thereto, metal associative groups, i.e., chelators, thiols, or the like.

Where the transparent material comprises a silica-based surface, silanes (e.g., methoxy-, or ethoxy-, silane reagents) can form stable bonds with silica surfaces via Si—O—Si bond formation, and are less reactive to metal or metal oxide surfaces such as aluminum or aluminum oxide surfaces under appropriately selected reaction conditions (e.g., vapor phase, solution-based treatments). Silanes, for example, silanes modified with coupling groups for attachment of enzymes or other molecules of interest (e.g., biotin-PEG-silanes such as those described in U.S. patent application Ser. No. 11/240, 662), can thus be used to bind desired molecules to silica surfaces such as those in a ZMW.

In some cases, the coupling groups are activatable or deactivatable coupling groups. A variety of different activatable or deactivatable coupling groups may be used in conjunction with this aspect of the invention. Typically, such groups include coupling groups that are capped or blocked with a selectively removable group. These include groups that are thermally altered, e.g., thermolabile protecting groups, chemically altered groups, e.g., acid or base labile protecting groups, and photo alterable groups, e.g., photo-cleavable or removable protecting groups. Suitable activatable and deactivatable coupling groups are provided, for example, in U.S. patent application Ser. No. 11/394,352.

A variety of different coupling groups may be used in this context, depending upon the nature of the molecule of interest to be subsequently deposited upon and coupled to the substrate. For example, the coupling groups may include functional chemical moieties, such as amine groups, carboxyl groups, hydroxyl groups, sulfhydryl groups, metals, chelators, and the like. Alternatively or additionally, they may include specific binding elements, such as biotin, avidin, streptavidin, neutravidin, lectins or SNAP-tags™ and their substrates (Covalys Biosciences AG; the SNAP-tag™ is a polypeptide based on mammalian O6-alkylguanine-DNA-alkyltransferase, and SNAP-tag substrates are derivates of benzyl purines and pyrimidines), associative or binding peptides or proteins, antibodies or antibody fragments, nucleic acids or nucleic acid analogs, or the like. Click chemistry including the Azide-Alkyne Huisgen Cycloaddition catalyzed, for example, by copper can also be used.

Additionally, or alternatively, the coupling group may be used to couple an additional group that is used to couple or bind with the molecule of interest, which may, in some cases include both chemical functional groups and specific binding elements. One set of embodiments utilizes biotin to attach a molecule of interest to the silica-based or transparent substrate. The attachment of biotin or other selective binding group to the surface can be accomplished in a number of ways.

One exemplary approach involves reacting a silica-based surface region with a compound having a silane group directly coupled to the selective binding group, for example, a silane-polyethylene glycol-biotin compound to produce a surface having selective binding groups, e.g. biotin bound to the silica-based region. This method provides a one step process for obtaining a silica-based surface having selective binding groups such as biotin attached thereto. In some cases, the silane compound having the selective binding group is diluted with a silane that does not contain the selective binding group, e.g. silane-polyethylene glycol in order to control the density of selective binding groups on the silica-based surface.

Another exemplary approach involves first reacting the surface with a coupling agent, and reacting the coupling agent on the surface with an attaching agent that has both functionality for reacting with the coupling agent, and functionality for attaching the desired molecule (e.g. a selective binding agent such as biotin). For example, the silica-based surface is reacted with an aminosilane or thiol-silane under conditions where the aminosilane or thiol-silane becomes bound to the substrate. The aminosilane or thiol-silane surface is subsequently reacted with an attaching agent, for example having an activated ester coupled to biotin to link the biotin to the aminosilane surface, or a maleimide group coupled to biotin to link to the thiol-silane surface. The attaching agent can be diluted as described herein with molecules that react, for example, with the aminosilane or thiol-silane, but do not have selective binding groups. This process incorporating an attaching group results in the coupling the selective binding agent to the surface in two steps. While this approach uses two steps rather than the one step described above, it can have some advantages in development, processing, and quality control.

The linking chemistry between the coupling agent and the compound having the selective binding agent can comprise any suitable linking chemistry. The linking chemistry can comprise, for example, thiol-maleimide, anhydride-amine, alkyne-azide, epoxide-amine, or amine-activated ester. As with the one step method, the compound having the selective binding agent can be diluted with a compound with the same reactive functionality, but not having the selective binding agent to control the density of selective binding agent on the surface.

Labels on the Nucleotide or Nucleotide Analog

As discussed, various polymerases of the invention can incorporate one or more nucleotide analogs into a growing oligonucleotide chain. Upon incorporation, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" (or "nucleotide analogue") herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue. The systems and methods of the invention are generally applicable to either nucleotides or nucleotide analogs. Where the specification describes methods using nucleotides, unless it is specifically stated, it is to be understood that such method can also be used with nucleotide analogs.

In one useful aspect of the invention, nucleotide analogs can also be modified to achieve any of the improved properties desired. For example, various linkers or other substituents can be incorporated into analogs that have the effect of reducing branching fraction, improving processivity, or altering rates. Modifications to the analogs can include extending the phosphate chains, e.g., to include a tetra-, penta-, hexa- or heptaphosphate group, and/or adding chemical linkers to extend the distance between the nucleotide base and the dye molecule, e.g., a fluorescent dye molecule. Substitution of one or more non-bridging oxygen in the polyphosphate, for example with S or $BH_3$, can change the polymerase reaction kinetics, e.g., to achieve a system having two slow steps as described herein below. Optionally, one or more, two or more, three or more, or four or more non-bridging oxygen atoms in the polyphosphate group of the analog has a sulfur (S) substituted for an oxygen (O). While not being bound by theory, it is believed that the properties of the nucleotide, such as the metal chelation properties, electronegativity, or steric properties, can be altered by substitution of the non-bridging oxygen(s).

Many nucleotide analogs are available and can be incorporated by the polymerases of the invention. These include analog structures with core similarity to naturally occurring nucleotides, such as those that comprise one or more substituent on a phosphate, sugar or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in U.S. patent application Ser. No. 11/241,809, filed Sep. 29, 2005, and incorporated herein by reference in its entirety for all purposes. Other exemplary useful analogs, including tetraphosphate, pentaphosphate, and hexaphosphate analogs, are described in U.S. Pat. Nos. 7,041,812 and 7,405,281 incorporated herein by reference in their entirety for all purposes.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc. and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., U.S. Patent Application Publication No. 2003/0124576, previously incorporated herein by reference in its entirety for all purposes.

Additional details regarding analogs and methods of making such analogs can be found in U.S. patent application Ser. No. 11/241,809, filed Sep. 29, 2005, and incorporated herein by reference in its entirety for all purposes.

Thus, in one illustrative example, the analog can be a phosphate analog (e.g., an analog that has more than the typical number of phosphates found in nucleoside triphosphates) that includes, e.g., an Alexa dye label. For example, an Alexa488 dye can be labeled on a delta phosphate of a tetraphosphate analog (denoted, e.g., A488dC4P or A488dA4P, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C or A568dT6P for a labeled hexaphospate analog of T), or an Alexa546 dye can be used (e.g., A546dG4P), or an Alexa594 dye can be used (e.g., A594dT4P). As additional examples, an Alexa555 dye (e.g., A555dC6P or A555dA6P), an Alexa 647 dye (e.g., A647dG6P), an Alexa 568 dye (e.g., A568dT6P), and/or an Alexa660 dye (e.g., A660dA6P or A660dC6P) can be used in, e.g., single molecule sequencing. Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

Alternative labeling strategies may employ inorganic materials as labeling moieties, such as fluorescent or luminescent nanoparticles, e.g. nanocrystals, i.e. Quantum Dots, that possess inherent fluorescent capabilities due to their semiconductor make up and size in the nanoscale regime (See, e.g., U.S. Pat. Nos. 6,861,155, 6,699,723, 7,235,361). Such nanocrystal materials are generally commercially available from, e.g., Molecular Probes, (Oregon). Again, such compounds may be present as individual labeling groups or as interactive groups or pairs, e.g., with other inorganic nanocrystals or organic fluorophores.

Initiation of the Reaction

When monitoring a reaction within an optical confinement it can be desirable to control the initiation of the reaction. For instance, a molecule of interest such as a catalyst or enzyme may be immobilized within an optical confinement on a substrate, the optical confinement can then be placed into contact with a reaction solution under conditions where the reaction will not occur. The substrate is then placed into a measurement system and aligned. When the system is ready to observe the reaction, the reaction is initiated.

Initiation of the reaction can be accomplished by adding a reagent that is lacking, for example, a substrate, cofactor, or metal ion. The reaction can also be initiated by changing the conditions, such as the pH, concentration, humidity, or temperature of the reaction. For polymerase enzymes, various methods for initiating the polymerase reaction are known. In some cases, hot-start polymerase enzyme systems are used. In some cases, the polymerase enzyme reaction can be initiated by the addition of a metallic cofactor such as Mn++ or Mg++.

Halting the Sequencing Reaction—Inhibitors

One aspect of the invention involves halting a reaction which is being observed so that the optical waveguide can be observed while the reaction is not occurring to obtain sticking data. Measurement while the reaction is not occurring can be used to can be used as described herein to improve the quality of the information obtained while observing the reaction occurring. Halting the reaction can be accomplished by adding a compound which inhibits the enzyme or catalyst. Alternatively, halting the reaction can be accomplished by adding a compound that complexes with, precipitates, or degrades a reagent that is necessary for the reaction such as a substrate, cofactor, or metal ion. The reaction can also be halted by changing the conditions, such as the pH, concentration, humidity, or temperature of the reaction. It is generally desired that the conditions used to halt the reaction do not have a substantial effect on the background of the reaction, such that the information obtained while the reaction is halted is most representative of the background present while the reaction was occurring. For example, it can be desirable that the addition of a reagent to inhibit or halt the reaction result in a small level of dilution of labeled compounds within the reaction solution. In some cases it is desired that the reaction be diluted by less than 1%, less than 2%, less than 5%, less than 10%, less that 15%, less than 20%, less than 25% or less than 50% of the concentration prior to halting the reaction.

Where the active single molecule comprises an enzyme, enzyme inhibitors, which are well known in the art can be used. Enzyme inhibitors include molecules that bind to enzymes and decrease their activity. Since blocking an enzyme's activity can kill a pathogen or correct a metabolic imbalance, many drugs are enzyme inhibitors. Many herbicides and pesticides are also inhibitors. Not all molecules that bind to enzymes are inhibitors; enzyme activators bind to enzymes and increase their enzymatic activity.

The binding of an inhibitor can stop a substrate from entering the enzyme's active site and/or hinder the enzyme from catalyzing its reaction. Inhibitor binding is either reversible or irreversible. Irreversible inhibitors usually react with the enzyme and change it chemically. These inhibitors often modify key amino acid residues needed for enzymatic activity. In contrast, reversible inhibitors generally bind non-covalently, and different types of inhibition are produced depending on whether these inhibitors bind the enzyme, the enzyme-substrate complex, or both. When reversible inhibitors are used, in some cases an inhibitor reversal agent can be added to reverse the inhibition. In some cases, the fluid in contact with the active molecules is replaced to wash out the inhibitor, adding back the necessary components for the reaction, thus reversing the inhibition.

Enzyme inhibitors also occur naturally and are involved in the regulation of metabolism. For example, enzymes in a metabolic pathway can be inhibited by downstream products. This type of negative feedback slows flux through a pathway when the products begin to build up and is an important way to maintain homeostasis in a cell. For example, polymerase enzymes produce pyrophosphate, and thus pyrophosphate and other phosphates, phosphonates, and polyphosphates can be used to inhibit the polymerase enzyme. In some cases, polyphosphate buffer can be used to inhibit the enzyme.

Other enzyme inhibitors are proteins that specifically bind to and inhibit an enzyme target. This can help control enzymes that may be damaging to a cell, such as proteases or nucleases; a well-characterized example of an inhibitor is the ribonuclease inhibitor, which binds to ribonucleases in one of the tightest known protein-protein interactions. In some cases, an antibody that binds to the polymerase enzyme can be used as an inhibitor. In some cases, heparin can be used to inhibit the active single molecule such as a polymerase.

Suitable inhibitors include chelating agents that can chelate with metals cofactors for an enzyme, such as a chelators for magnesium or manganese required by a polymerase enzyme. Suitable chelators include polyamine chelators such as ethylenediaminetetraacetic acid (EDTA) or carboxylate chelators such as ethylene glycol tetraacetic acid (EGTA) or 1,2-bis(o-aminophenoxy)ethane-N,N,N',N'-tetraacetic acid (BAPTA) In some cases, temperature or pH can be used alone or in combination to provide inhibition of the enzyme. In some cases, native nucleotides can competitively inhibit. In some cases, blocked nucleotides such as dideoxy NTPs can inhibit the reaction by terminating synthesis. In some cases, nucleotide analogs that are reversibly blocked can be used as reversible inhibitors.

In addition, the determination of whether a compound is an inhibitor of an enzyme can be determined by methods well known in the art without a unreasonable amount of experimentation. For example, enzyme assays are generally performed to determine the activity of enzymes. By performing side by side reactions with and without potential inhibitors, the determination of whether a compound is an inhibitor and under what concentration that the compound will effectively inhibit the enzyme can be made.

Where the molecule of interest in the optical confinement is a nucleic acid polymerase, a polymerase inhibitor can be used to halt the reaction. There are several known DNA-dependent DNA polymerase inhibitors known in the art. For example, Actinomycin-D acts as a DNA-dependent DNA polymerase inhibitor by binding to DNA and preventing initiation of replication (Guy and Taylor (1978) PNAS 75:6088-92.) Other examples of DNA-dependent DNA polymerase inhibitors include, but are not limited to, actinomycin (dactinomycin), alpha-amanitin, aphidicolin (Cozad and Warner (1982) Gamete Research 6:155-60; Gonzcol and Plotkin (1985) Arch Virology 84:129-34; Haraguchi et al. (1983) Nucleic Acids Research 11:1197-1209), BPS, novobiocin (Schneck and Staudenbauer (1977) Nuc Acids Res 4:2057-64), rifampicin, rifamycin (Frolova et al. (1977) Nuc Acids Res 4:523-8), sulfoquinovosylmonoacylglycerol, sulfoquinovosyldiacylglycerol (Ohta et al. (2000) Mutat Res 467: 139-52; Ohta et al. (1999) Biol Pharm Bull 22:111-16), ursane, oleanane, triterpenoids, ursolic acid, oleanolic acid (Deng et al. (1999) J Nat Prod 62:1624-6), mikanolide, dihydromikanolide (U.S. Pat. No. 6,767,561), dehydroaltenusin (Mizushina et al. (2000) J Biol Chem 275:33957-61), catapol (Pungitore et al. (2004) J Nat Prod 67:357-61), taxinine, cephalomanninine (Oshige et al. (2004) Bioorganic and Medicinal Chem 12:2597-601), dipeptide alcohols (Kato et al. (2005) Int J Mol Med 16:653-9), corylifolin; bakuchiol; resveratrol; Neobavaisoflavone; daidzein; bakuchicin (Sun et al. (1998) J Nat Prod 61:362-6), levodopa, dopamine (Wick (1980) Cancer Research 40:1414-8), anacardic acid and oleic acid (Chen et al. (1998) Chem Comm 24:2769-70). Suitable inhibitors include $N^2$-(p-n-butylphenyl) dGTP (BuPdGTP) and 2-(p-n-butylanilino) dAPT (BuAdAPT).

DNA polymerase inhibitors of the present invention are added in an amount effective to inhibit DNA polymerase activity. As a result, replication of DNA, when present in the sample in combination with RNA target or targets, is inhibited. The amount of a DNA polymerase inhibitor that should be added to achieve the desired inhibition is well known and understood in the art. For example, the DNA polymerase inhibitor Actinomycin D may be added in a concentration from about 0.1 μg/ml to about 100 μg/ml. In a preferred embodiment, 50% of DNA replication is inhibited by addition of a DNA polymerase inhibitor. In another preferred embodiment, 60% of DNA replication is inhibited by addition of a DNA polymerase inhibitor. In yet other preferred embodiments, 70%, 80%, 85%, 90%, 95%, 96%, 97%, 98%, 99% or 100% of DNA replication is inhibited by addition of a DNA polymerase inhibitor.

Combinations of DNA polymerase inhibitors may be used to achieve the desired inhibition. Use of combinations of DNA polymerase inhibitors may be desirable to minimize unwanted effects on the reaction conditions by decreasing the concentration of each inhibitor in the reaction mixture. Alternatively, the combination of inhibitors may be able to achieve a greater amount of inhibition, such as by inhibiting DNA polymerase activity at various stages. RNA polymerase inhibitors can be used for the monitoring of the reaction of RNA polymerases. Suitable RNA polymerase inhibitors are described, for example, in U.S. Pat. No. 6,906,190B2, US20040023921A1, US20030224469A1, US20060183751 A1, US20060183111 A1, US20060074035A1, US20030037355A1, U.S. Pat. No. 6,322,966B1, which are incorporated by reference in their entirety herein.

In some embodiments, the halting of the reaction is reversible, allowing for measuring sticking data then re-starting the reaction to continue to monitor the reaction, e.g. continue to collect sequencing data. In some cases, the methods described above for initiating the reaction can be used to re-start the reaction after halting it. Reversible inhibitors can bind to enzymes with non-covalent interactions such as hydrogen bonds, hydrophobic interactions, and ionic bonds. Multiple weak bonds between the inhibitor and the active site combine to produce strong and specific binding. In contrast to substrates and irreversible inhibitors, reversible inhibitors generally do not undergo chemical reactions when bound to the enzyme and can be removed, for example by dilution or dialysis. In some embodiments, chelating agents can be used as reversible inhibitors. The enzyme activity can be restored by flushing out the chelating agent and adding back the metals required for activity.

Combining Sticking Data

An aspect of the invention is combining the data that is obtained while the reaction is not occurring, the sticking data, with the data that is obtained during the reaction to improve the quality of the information obtained about the reaction during the reaction. There are a number of ways in which the sticking data can be combined with the data taken during the reaction. The sticking data can be used, for example, to correct the reaction data, to exclude the reaction data or portions of the data, or to provide a weighting or confidence level to the data for combining the data with other data.

Both reaction data and sticking data are generally obtained for each optical confinement, and for each optical channel. The data obtained while the reaction is not occurring provides information about the characteristics of each specific optical confinement, and each optical channel within that optical confinement. In some cases, that optical confinement will have higher or lower background intensity than other optical confinements that can be corrected for by measuring the ZMW when the reaction is stopped.

In some cases, multiple optical channels are monitored concurrently within each optical confinement. For example, when sequencing, four optical channels may be used to observe each of four labels, one for each type of nucleotide or nucleotide analog. We have found that the optical behavior within each channel can vary significantly in addition to the variation of optical behavior between optical confinements, Not only have we observed significant variation, but we have found that the optical behavior will fall in many cases into a certain pattern or type, making it possible to correct for the behavior by, for example compensating or correcting the data obtained from the in the optical confinement or ZMW during the reaction. When performing sequencing, we have found that a significant source of error falls into the category we describe as stickiness. As described above, stickiness can occur when labeled reactants, such as labeled nucleotides or nucleotide analogs, either adsorb non-specifically within the optical confinement or bind to the active site of the polymerase without being incorporated. In some cases, stickiness can be caused by or exacerbated by other phenomenon within the optical system, such autofluorescence, or noise in the optical detectors. A characteristic of stickiness is that it is generally present whether a reaction is occurring or not. Thus, stickiness can be caused by non-specific adsorption of labeled compounds within the observation volume of the optical confinement, but it is not limited to signals from this source. Thus stickiness represents a source of error that can be reduced or eliminated by employing the sticking data as described herein.

Figure 5:
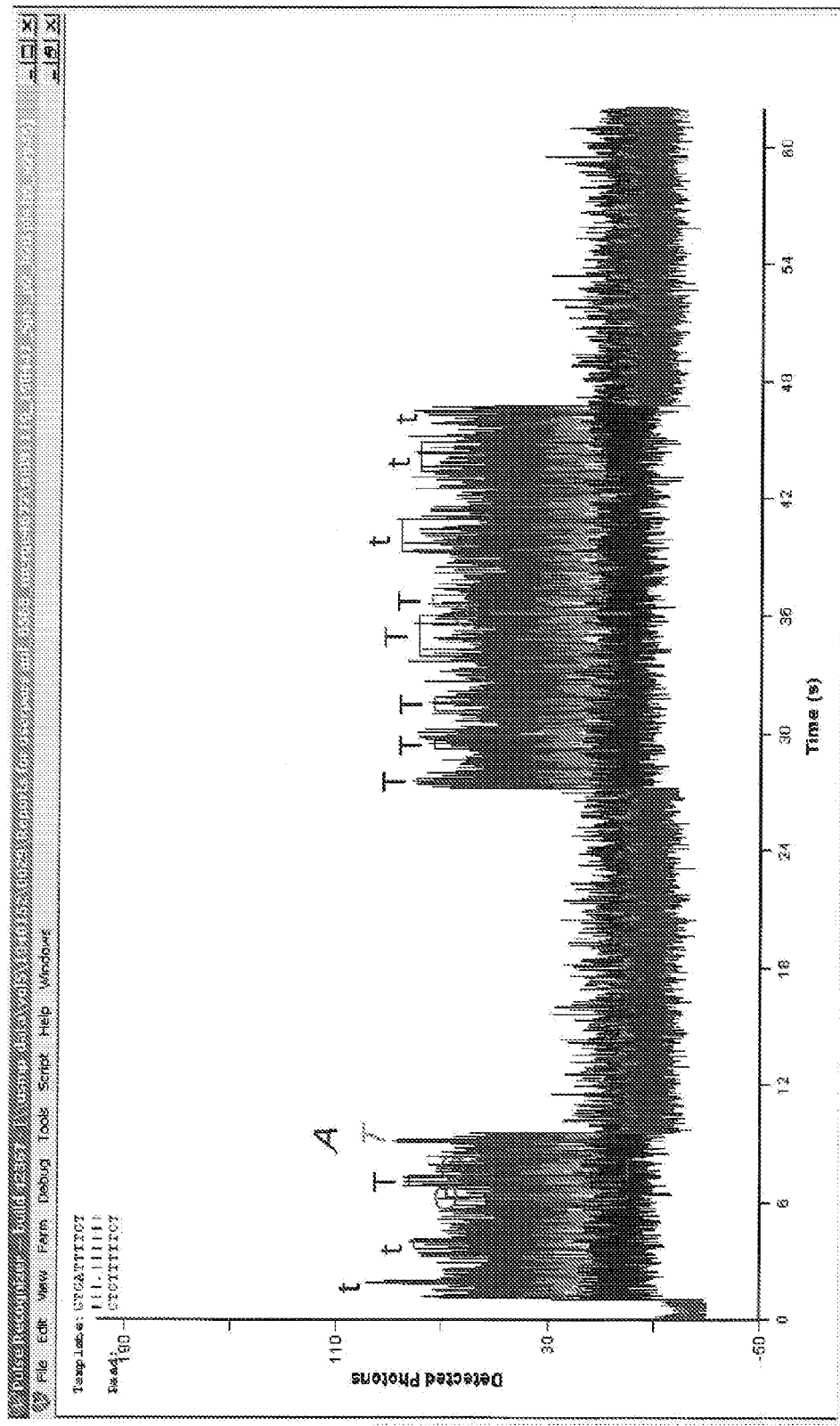
FIGS. 5-8 shows plots of detected photons per time, each for a single optical confinement showing the sticking behavior in that optical confinement.

FIG. 5 shows an example of fluorescence emission data from a zero-mode waveguide in which no sequencing reaction is occurring. The reaction mixture comprises 4 labeled nucleotide analogs corresponding to nucleotides A, G. T, and C, each with a separately observable dye attached to the end of its polyphosphate tail. Photons are detected in all 4 of the optical channels. FIG. 5 shows that there are periods of time in which a multiple pulses are observed that are characteristic of the dye corresponding to a T. Before and after these periods of time, there are time periods having a normal background signal with no extra sticking peaks. During this time period, there are very few sticking peaks in the channels correlating to the nucleotides A, G, and C. Where sticking data shows this type of sticking characteristics, the data can be used to improve the quality of the data from this ZMW. The reaction data from the T channel can be corrected by subtracting out regions having this characteristic. In some cases, the data from the T channel can be removed from the analysis, or the data can be given a lower weight or confidence level than similar data from other ZMWs. By correcting the data, eliminating the results, or providing weighting to the data, the quality of the sequencing data can be improved.

Figure 6:
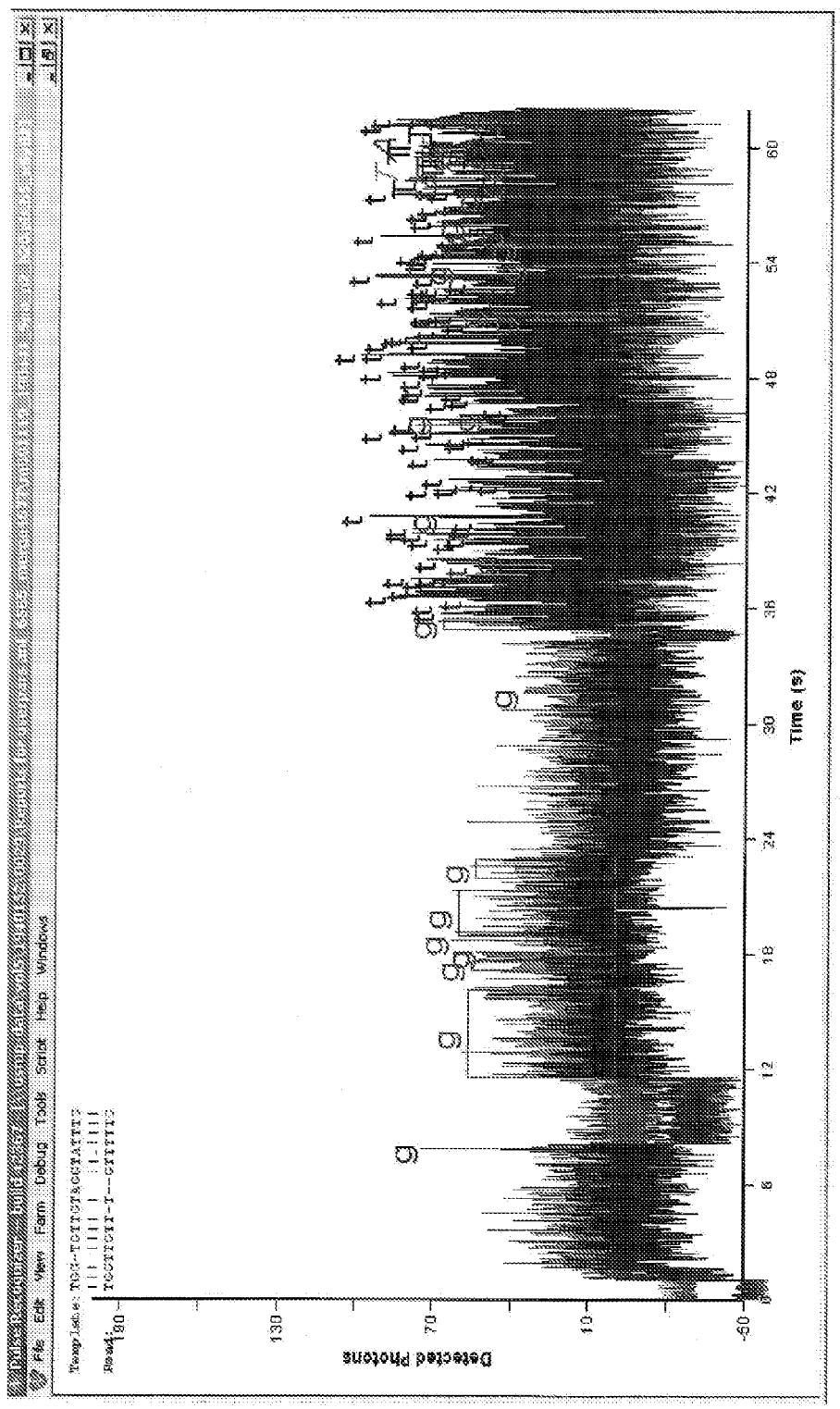
Figure 7:
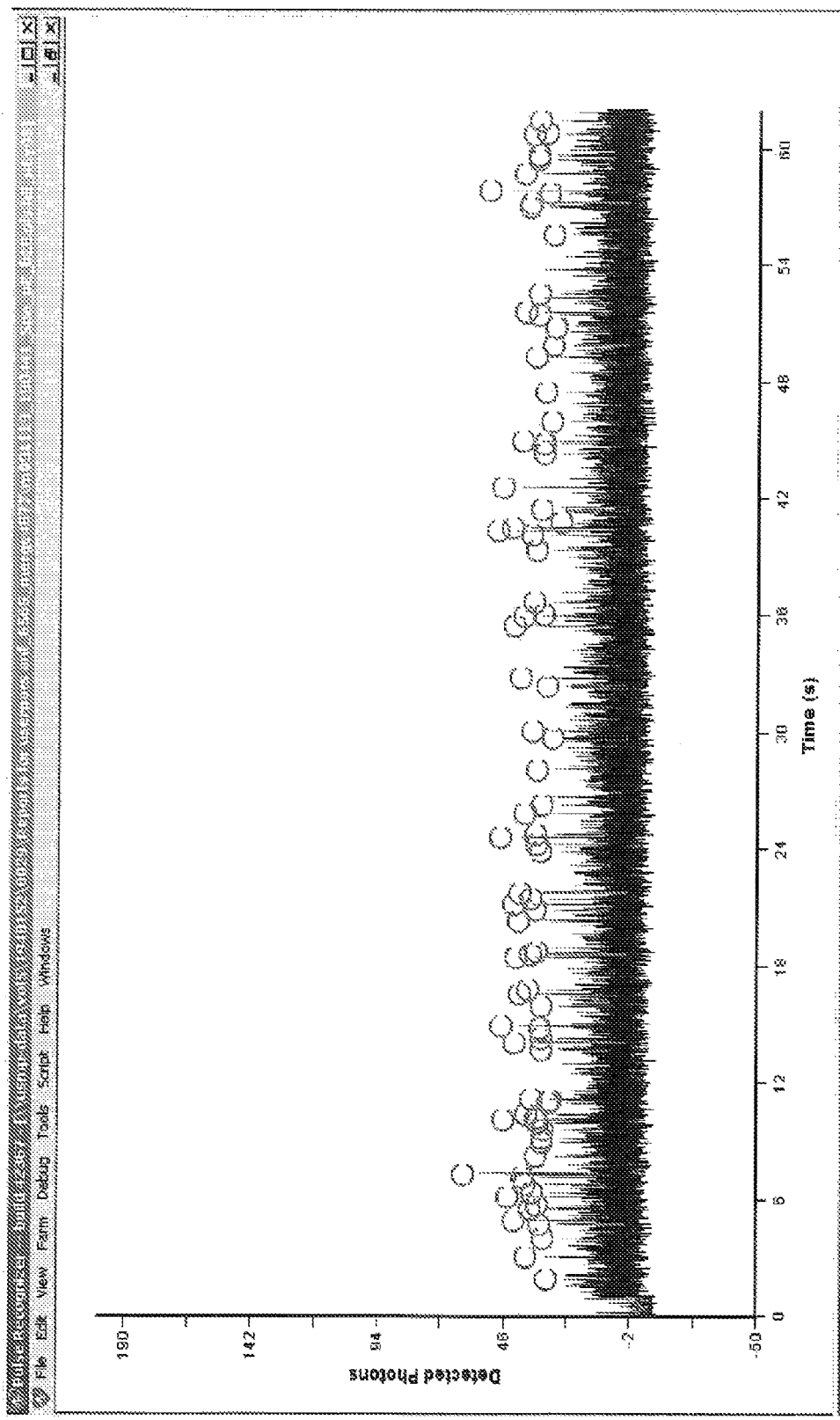
Figure 8:
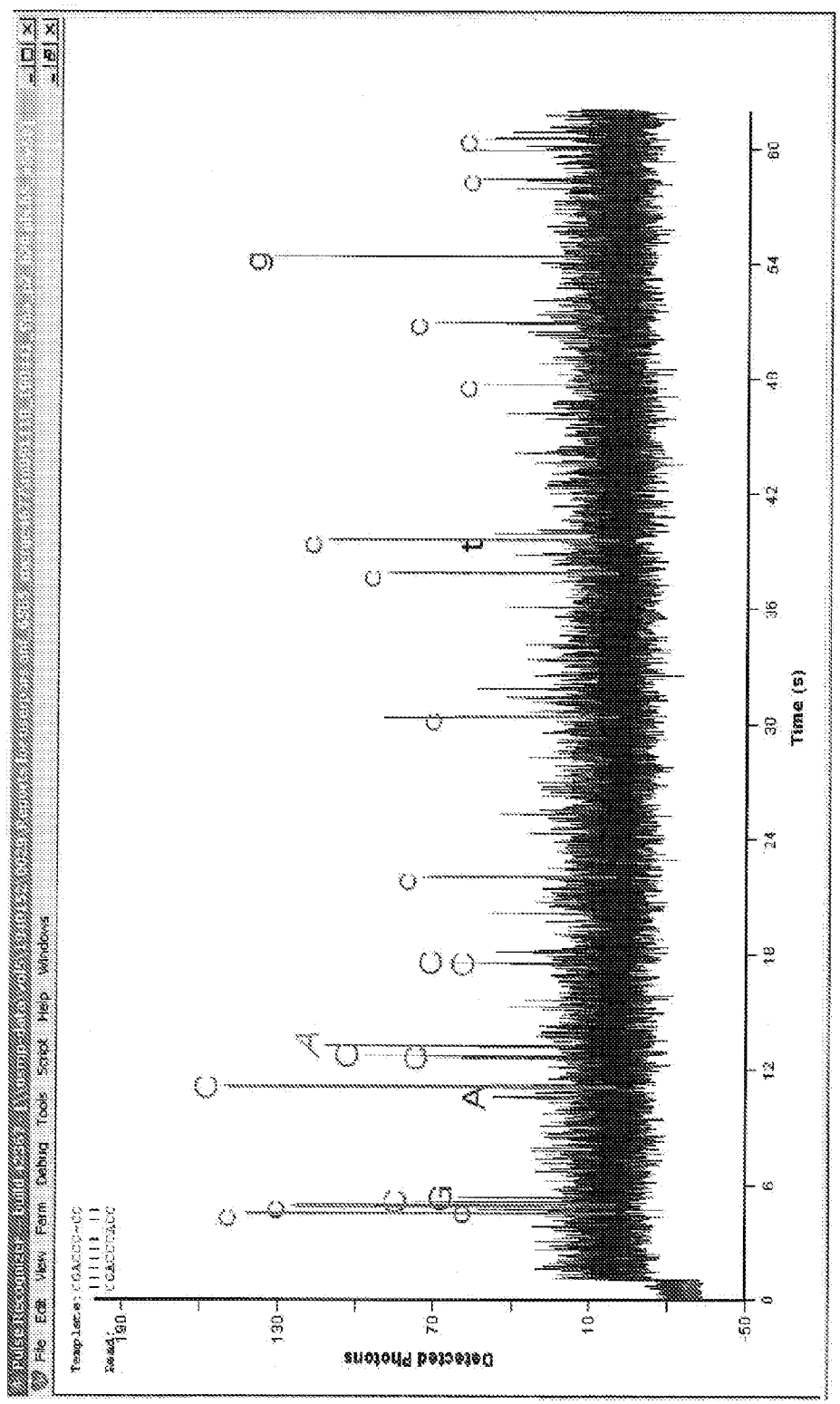

FIGS. 6-8 show other characteristic sticking patterns that have been observed. FIG. 6 shows a pattern in which there are regions of sticking peaks corresponding to G, and regions of sticking peaks corresponding to T. FIG. 7 shows a case in which the ZMW shows random sparse peaks corresponding to C. FIG. 8 shows a pattern in which a number of C peaks are observed as well as some peaks from A, T, and G at a lower frequency. As described above in reference to FIG. 5, the data from traces such as those shown in FIGS. 6-8 can be used to improve the reaction data for the ZMWs that correspond to these traces, for example to correcting the data, eliminating the results, or providing weighting to the data as it is combined with other sequencing data.

The sticking data and the reaction data are measured over time. For nucleic acid sequencing, the time period over which the data is obtained is generally in the range of seconds to hours. The time period over which the sticking data is obtained can be different than the time period over which reaction data is obtained. The time period over which sticking data is obtained is generally less than the time period over which reaction data is obtained.

Base Calling and Sequence Determination

Figure 9:
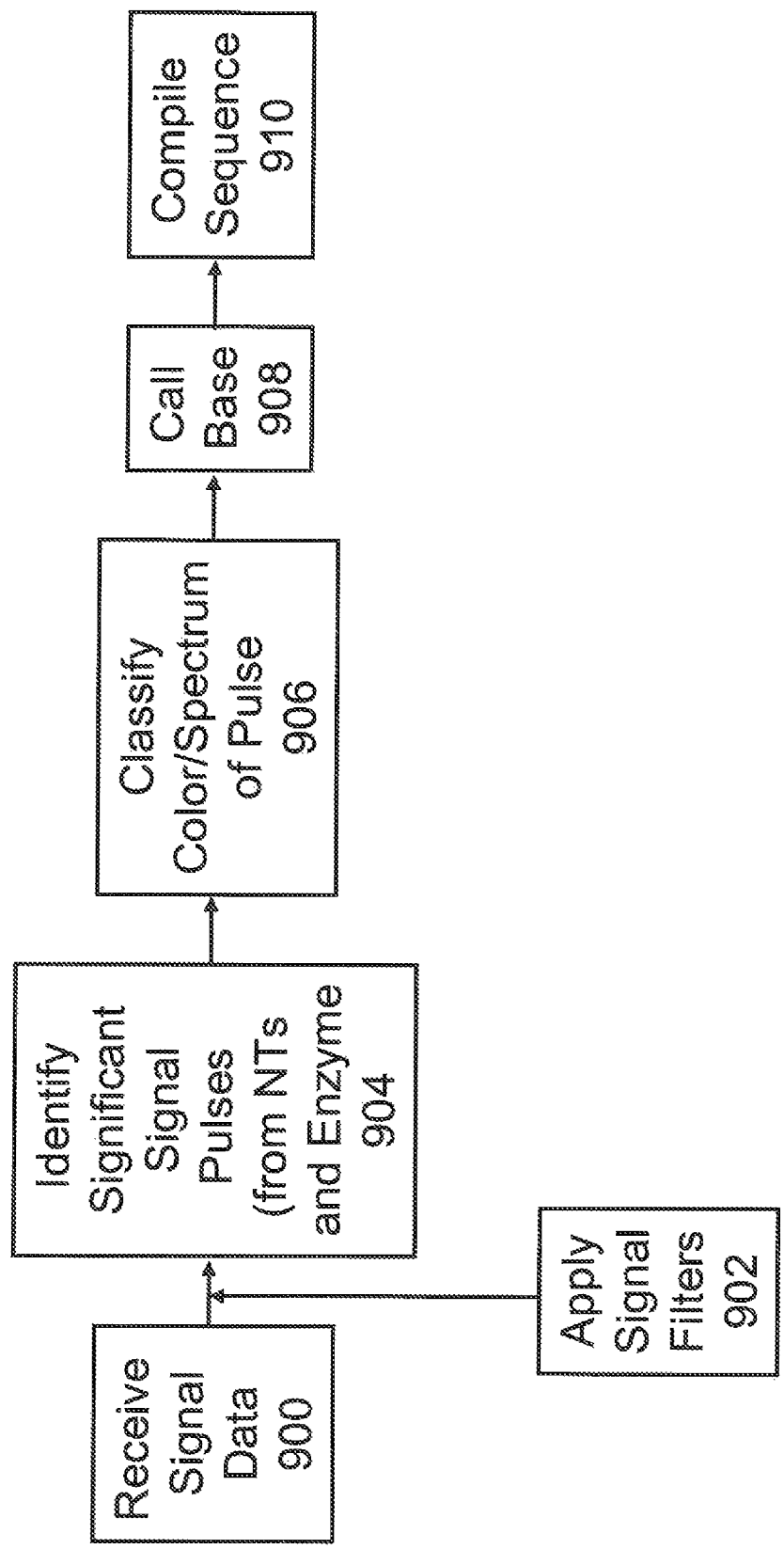
FIG. 9 is a flow chart of a process for producing sequencing information from signal data.

The systems and methods of the inventions can result in improved sequence determination and improved base calling by using information from the labeled nucleotides along with concurrent information from the labeled protein indicating the conformation of the protein. A general flow chart illustrating an embodiment of a base calling and sequence determination process using such signal data is provided in FIG. 9. In general, signal data is received by the processor at step 900. The information received by the processor can come directly from the detection optics, or the signal from the detection optics can be treated by other processors before being received by the processor at step 900. A number of initial calibrations operations may be applied at step 902. Some of these initial calibration steps may be performed just once at the beginning of a run or on a more continuous basis during the run. These initial calibration steps can include such things as centroid determination, alignment, gridding, drift correction, initial background subtraction, noise parameter adjustment, frame-rate adjustment, etc. Some of these initial calibration steps, such as binning, may involve communication from the processor back to the detector/camera, as discussed further below.

Generally, some type of spectral trace determination/spectral trace extraction/spectral filters are applied to the initial signal data at step 902. Some or all of this filter step may optionally be carried out at a later point in the process, e.g., after the pulse identification step 904. The spectral trace extraction/spectral filters may include a number of noise reduction and other filters as set forth elsewhere herein. Spectral trace determination is performed at this stage for many of the example systems discussed herein because the initial signal data received are the light levels, or photon counts, captured by a series of adjacent pixel detectors. For example, in one example system, 14 pixels (or intensity levels) from 14 positions are captured for an individual wave-guide at each frame. Light of different frequencies or spectrum will fall on more than one of the 14 positions and there is generally some overlap and possibly substantial overlap. According to specific embodiments of the invention, spectral trace extraction may be performed using various analysis, as discussed below, that provide the highest signal-to-noise ratio for each spectral trace.

As an alternative to a spectral trace determination, methods of the invention may also analyze a single signal derived from the intensity levels at the multiple pixel positions (this may be referred to as a summed spectral signal or a gray-scale spectral signal or an intensity level signal). In many situations, it has been found that spectral extraction, however, provides better SNR and therefore pulse detection when extracted spectral traces are analyzed for pulses somewhat separately. In further embodiments, a method according to the invention may analyze the multiple captured pixel data using a statistical model such as a Hidden Markov Model. In present systems, however, determining multiple (e.g., four) spectral traces from the initial signal data has proven a preferred method.

Whether the signal from the labels on the nucleotides or the label or labels on the polymerase can be categorized as a significant signal pulse or event is determined at step 904. In some example systems, because of the small number of photons available for detection and because of the speed of detection, various statistical analysis techniques may be performed in determining whether a significant pulse has been detected.

If the signal is identified as a significant pulse or signal event at step 904, a further optional spectral profile comparison may be performed to verify the spectral assignment. This spectral profile comparison is optional in embodiments where spectral traces are determined prior to or during pulse identification. Once a color is assigned to a given incorporation signal, that assignment is used to call either the base incorporated, or its complement in the template sequence, at step 908. In order to make this determination, the signals from the channel corresponding to the label on the enzyme which is sensitive to enzyme conformation is used to assess whether a pulse from a nucleotide label corresponds to an incorporation event. The compilation of called bases is then subjected to additional processing at step 910, to provide linear sequence information, e.g., the successive sequence of nucleotides in the template sequence, assemble sequence fragments into longer contigs, or the like.

As noted above, the signal data is input into the processing system, e.g., an appropriately programmed computer or other processor. Signal data may input directly from a detection system, e.g., for real time signal processing, or it may be input from a signal data storage file or database. In some cases, e.g., where one is seeking immediate feedback on the performance of the detection system, adjusting detection or other experimental parameters, real-time signal processing will be employed. In some embodiments, signal data is stored from the detection system in an appropriate file or database and is subject to processing in post reaction or non-real time fashion.

The signal data used in conjunction with the present invention may be in a variety of forms. For example, the data may be numerical data representing intensity values for optical signals received at a given detector or detection point of an array based detector. Signal data may comprise image data from an imaging detector, such as a CCD, EMCCD, ICCD or CMOS sensor. In either event, signal data used according to specific embodiments of the invention generally includes both intensity level information and spectral information. In the context of separate detector elements, such spectral infoii-nation will generally includes identification of the location or position of the detector portion (e.g., a pixel) upon which an intensity is detected. In the context of image data, the spectral image data will typically be the data derived from the image data that correlates with the calibrated spectral image data for the imaging system and detector when the system includes spectral resolution of overall signals. The spectral data may be obtained from the image data that is extracted from the detector, or alternatively, the derivation of spectral data may occur on the detector such that spectral data will be extracted from the detector.

For the sequencing methods described above, there will be a certain amount of optical signal that is detected by the detection system that is not the result of a signal from an incorporation event. Such signal will represent "noise" in the system, and may derive from a number of sources that may be internal to the monitored reaction, internal to the detection system and/or external to all of the above. Examples of noise internal to the reaction being monitored includes, e.g.: presence of fluorescent labels that are not associated with a detection event, e.g., liberated labels, labels associated with unincorporated bases in diffused in solution, bases associated with the complex but not incorporated; presence of multiple complexes in an individual observation volume or region; non-specific adsorption of dyes or nucleotides to the substrate or enzyme complex within an observation volume; contaminated nucleotide analogs, e.g., contaminated with other fluorescent components; other reaction components that may be weakly fluorescent; spectrally shifting dye components, e.g., as a result of reaction conditions; and the like. The use of information from the label on the polymerase sensitive to enzyme conformation provides a way of reducing or eliminating sources of noise, thereby improving the signal to noise of the system, and improving the quality of the base calls and associated sequence determination.

Sources of noise internal to the detection system, but outside of the reaction mixture can include, e.g., reflected excitation radiation that bleeds through the filtering optics; scattered excitation or fluorescent radiation from the substrate or any of the optical components; spatial cross-talk of adjacent signal sources; auto-fluorescence of any or all of the optical components of the system; read noise from the detector, e.g., CCDs, gain register noise, e.g., for EMCCD cameras, and the like. Other system derived noise contributions can come from data processing issues, such as background correction errors, focus drift errors, autofocus errors, pulse frequency resolution, alignment errors, and the like. Still other noise contributions can derive from sources outside of the overall system, including ambient light interference, dust, and the like.

These noise components contribute to the background photons underlying any signal pulses that may be associated with an incorporation event. As such, the noise level will typically form the limit against which any signal pulses may be determined to be statistically significant.

Identification of noise contribution to overall signal data may be carried out by a number of methods, including, for example, signal monitoring in the absence of the reaction of interest, where any signal data is determined to be irrelevant. Alternatively, and preferably, a baseline signal is estimated and subtracted from the signal data that is produced by the system, so that the noise measurement is made upon and contemporaneously with the measurements on the reaction of interest. Generation and application of the baseline may be carried out by a number of means, which are described in greater detail below.

In accordance with the present invention, signal processing methods distinguish between noise, as broadly applied to all non-significant pulse based signal events, and significant signal pulses that may, with a reasonable degree of confidence, be considered to be associated with, and thus can be tentatively identified as, an incorporation event. In the context of the present invention, a signal event is first classified as to whether it constitutes a significant signal pulse based upon whether such signal event meets any of a number of different pulse criteria. Once identified or classified as a significant pulse, the signal pulse may be further assessed to determine whether the signal pulse constitutes an incorporation event and may be called as a particular incorporated base. As will be appreciated, the basis for calling a particular signal event as a significant pulse, and ultimately as an incorporation event, will be subject to a certain amount of error, based upon a variety of parameters as generally set forth herein. As such, it will be appreciated that the aspects of the invention that involve classification of signal data as a pulse, and ultimately as an incorporation event or an identified base, are subject to the same or similar errors, and such nomenclature is used for purposes of discussion and as an indication that it is expected with a certain degree of confidence that the base called is the correct base in the sequence, and not as an indication of absolute certainty that the base called is actually the base in a given position in a given sequence.

One such signal pulse criterion is the ratio of the signals associated with the signal event in question to the level of all background noise ("signal to noise ratio" or "SNR"), which provides a measure of the confidence or statistical significance with which one can classify a signal event as a significant signal pulse. In distinguishing a significant pulse signal from systematic or other noise components, the signal generally must exceed a signal threshold level in one or more of a number of metrics, including for example, signal intensity, signal duration, temporal signal pulse shape, pulse spacing, and pulse spectral characteristics.

By way of a simplified example, signal data may be input into the processing system. If the signal data exceeds a signal threshold value in one or more of signal intensity and signal duration, it may be deemed a significant pulse signal. Similarly, if additional metrics are employed as thresholds, the signal may be compared against such metrics in identifying a particular signal event as a significant pulse. As will be appreciated, this comparison will typically involve at least one of the foregoing metrics, and preferably at least two such thresholds, and in many cases three or all four of the foregoing thresholds in identifying significant pulses.

Signal threshold values, whether in terms of signal intensity, signal duration, pulse shape, spacing or pulse spectral characteristics, or a combination of these, will generally be determined based upon expected signal profiles from prior experimental data, although in some cases, such thresholds may be identified from a percentage of overall signal data, where statistical evaluation indicates that such thresholding is appropriate. In particular, in some cases, a threshold signal intensity and/or signal duration may be set to exclude all but a certain fraction or percentage of the overall signal data, allowing a real-time setting of a threshold. Again, however, identification of the threshold level, in terms of percentage or absolute signal values, will generally correlate with previous experimental results. In alternative aspects, the signal thresholds may be determined in the context of a given evaluation. In particular, for example, a pulse intensity threshold may be based upon an absolute signal intensity, but such threshold would not take into account variations in signal background levels, e.g., through reagent diffusion, that might impact the threshold used, particularly in cases where the signal is relatively weak compared to the background level. As such, in certain aspects, the methods of the invention determine the background fluorescence of the particular reaction in question, including, in particular, the contribution of freely diffusing dyes or dye labeled analogs into a zero mode waveguide, and set the signal threshold above that actual background by the desired level, e.g., as a ratio of pulse intensity to background fluorophore diffusion, or by statistical methods, e.g., 5 sigma, or the like. By correcting for the actual reaction background, such as fluorophore diffusion background, the threshold is automatically calibrated against influences of variations in dye concentration, laser power, or the like. By reaction background is meant the level of background signal specifically associated with the reaction of interest and that would be expected to vary depending upon reaction conditions, as opposed to systemic contributions to background, e.g., autofluorescence of system or substrate components, laser bleedthrough, or the like.

In particularly preferred aspects that rely upon real-time detection of incorporation events, identification of a significant signal pulse may rely upon a signal profile that traverses thresholds in both signal intensity and signal duration. For example, when a signal is detected that crosses a lower intensity threshold in an increasing direction, ensuing signal data from the same set of detection elements, e.g., pixels, are monitored until the signal intensity crosses the same or a different intensity threshold in the decreasing direction. Once a peak of appropriate intensity is detected, the duration of the period during which it exceeded the intensity threshold or thresholds is compared against a duration threshold. Where a peak comprises a sufficiently intense signal of sufficient duration, it is called as a significant signal pulse.

In addition to, or as an alternative to using the intensity and duration thresholds, pulse classification may employ a number of other signal parameters in classifying pulses as significant. Such signal parameters include, e.g., pulse shape, spectral profile of the signal, e.g., pulse spectral centroid, pulse height, pulse diffusion ratio, pulse spacing, total signal levels, and the like.

Either following or prior to identification of a significant signal pulse, signal data may be correlated to a particular signal type. In the context of the optical detection schemes used in conjunction with the invention, this typically denotes a particular spectral profile of the signal giving rise to the signal data. In particular, the optical detection systems used in conjunction with the methods and processes of the invention are generally configured to receive optical signals that have distinguishable spectral profiles, where each spectrally distinguishable signal profile may generally be correlated to a different reaction event. In the case of nucleic acid sequencing, for example, each spectrally distinguishable signal may be correlated or indicative of a specific nucleotide incorporated or present at a given position of a nucleic acid sequence. Consequently, the detection systems include optical trains that receive such signals and separate the signals based upon their spectra. The different signals are then directed to different detectors, to different locations on a single array based detector, or are differentially imaged upon the same imaging detector (See, e.g., U.S. Patent Publication No. 2007/0036511, which is incorporated herein by reference in its entirety for all purposes).

In the case of systems that employ different detectors for different signal spectra, assignment of a signal type (for ease of discussion, referred to hereafter as "color classification" or "spectral classification") to a given signal is a matter of correlating the signal pulse with the detector from which the data derived. In particular, where each separated signal component is detected by a discrete detector, a signal's detection by that detector is indicative of the signal classifying as the requisite color.

In preferred aspects, however, the detection systems used in conjunction with the invention utilize an imaging detector upon which all or at least several of the different spectral components of the overall signal are imaged in a manner that allows distinction between different spectral components. Thus, multiple signal components are directed to the same overall detector, but may be incident upon wholly or partly different regions of the detector, e.g., imaged upon different sets of pixels in an imaging detector, and give rise to distinguishable spectral images (and associated image data). As used herein, spectra or spectral image generally indicates a pixel image or frame (optionally data reduced to one dimension) that has multiple intensities caused by the spectral spread of an optical signal received from a reaction location.

In its simplest form, it will be understood that assignment of color to a signal event incident upon a group of contiguous detection elements or pixels in the detector would be accomplished in a similar fashion as that set forth for separate detectors. In particular, the position of the group of pixels upon which the signal was imaged, and from which the signal data is derived, is indicative of the color of the signal component. In particularly preferred aspects, however, spatial separation of the signal components may not be perfect, such that signals of differing colors are imaged on overlapping sets of pixels. As such, signal identification will generally be based upon the aggregate identity of multiple pixels (or overall image of the signal component) upon which a signal was incident.

Once a particular signal is identified as a significant pulse and is assigned a particular spectrum, the spectrally assigned pulse may be further assessed to determine whether the pulse can be called an incorporation event and, as a result, call the base incorporated in the nascent strand, or its complement in the template sequence. In order to make the determination of incorporation, the signal from the label on the enzyme sensitive to enzyme conformation is used.

In addition, calling of bases from color assigned pulse data will typically employ tests that again identify the confidence level with which a base is called. Typically, such tests will take into account the data environment in which a signal was received, including a number of the same data parameters used in identifying significant pulses, etc. For example, such tests may include considerations of background signal levels, adjacent pulse signal parameters (spacing, intensity, duration, etc.), spectral image resolution, and a variety of other parameters. Such data may be used to assign a score to a given base call for a color assigned signal pulse, where such scores are correlative of a probability that the base called is incorrect, e.g., 1 in 100 (99% accurate), 1 in 1000 (99.9% accurate), 1 in 10,000 (99.99% accurate), 1 in 100,000 (99.999% accurate), or even greater. Similar to PHRED or similar type scoring for chromatographically derived sequence data, such scores may be used to provide an indication of accuracy for sequencing data and/or filter out sequence information of insufficient accuracy.

Once a base is called with sufficient accuracy, subsequent bases called in the same sequencing run, and in the same primer extension reaction, may then be appended to each previously called base to provide a sequence of bases in the overall sequence of the template or nascent strand. Iterative processing and further data processing can be used to fill in any blanks, correct any erroneously called bases, or the like for a given sequence.

Figure 10:
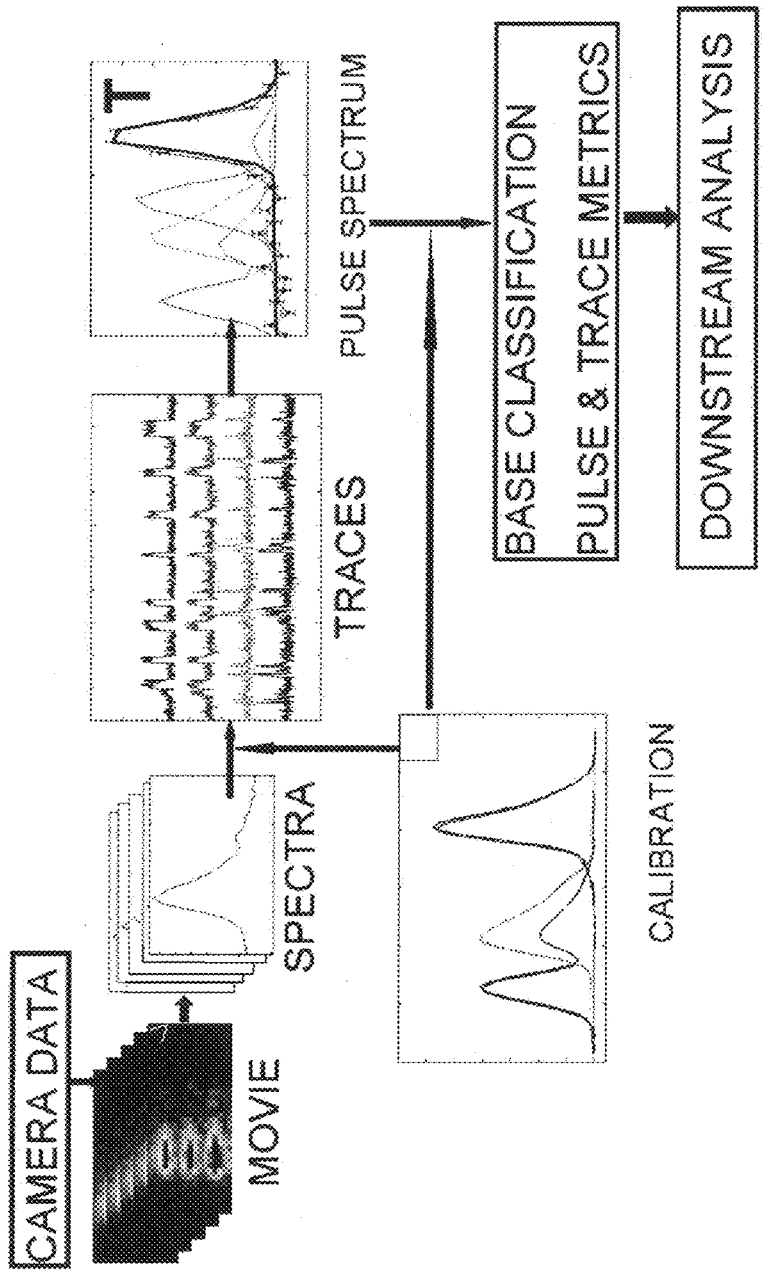
FIG. 10 shows a process for the analysis of sequencing data.

Analysis of sequencing-by-incorporation-reactions on an array of reaction locations according to specific embodiments of the invention is also illustrated graphically in FIG. 10. In this summary figure, data captured by a camera is represented as a movie, which is also a time sequence of spectra. Spectral calibration templates are used to extract traces from the spectra. Pulses identifies in the traces are then used to return to the spectra data and from that data produce a temporally averaged pulse spectrum for each pulse, such pulse spectra will include spectra for events relating to enzyme conformational changes. The Spectral calibration templates are then also used to classify pulse spectrum to a particular base. Base classifications and pulse and trace metrics are then stored or passed to other logic for further analysis. The downstream analysis will include using the information from enzyme conformational changes to assist in the determination of incorporation events for base calling. Further base calling and sequence determination methods for use in the invention are described in copending U.S. patent application Ser. No. 12/134,186, filed Jun. 5, 2008.

Systems

The invention comprises systems for sequencing of nucleic acid templates. The systems provide for concurrently sequencing a plurality of nucleic acid templates. The system can incorporate all of the reagents and methods described herein, and provides the instrumentation required for containing the sample, illuminating the sample with excitation light, detecting light emitted from the sample during sequencing to produce intensity versus time data from the labeled nucleotides and from the label indicative of enzyme conformation, and determining the sequence of a template using the intensity versus time data. The systems are capable of observing the sequencing reaction while it is occurring and after it is halted.

In some aspects, the system comprises an analysis instrument comprising: a substrate comprising optical confinements having a plurality of active molecules localized therein whereby a plurality of the optical confinements comprise a single active molecule; the substrate having a substrate reservoir which allows for exposing the single active molecules in the optical confinements to a reagent solution, whereby either the single active molecules or a reagent in the reagent solution or both comprise one or more fluorescent labels; an optical system for measuring fluorescence from the plurality of optical confinements over time to monitor the reaction and to obtain reaction data from each of the plurality of confinements and for measuring fluorescence from the plurality of optical confinements over time while the reaction is halted to obtain sticking data; a flow-cell in fluidic contact with the substrate for delivering agents to halt the reaction without moving the substrate; and a computer for combining the sticking data with reaction data.

The single active molecules can be localized within the optical confinements, for example, as described in copending U.S. patent application Ser. No. 12/384,097 filed Mar. 30, 2009 which is incorporated herein in its entirety by reference for all purposes. In some cases, not all of the optical confinements on the substrate will have a single active molecule. The reagent solution which is brought into contact with the substrate can be held in place, for example, by a substrate reservoir. In some cases, the reservoir is formed by a chip which holds the substrate at the bottom, and has sidewalls to hold the fluid. Suitable packages comprising arrays of optical confinements are described, for example, in U.S. Provisional Patent Application 61/261,212 filed Nov. 13, 2009 which is incorporated herein in its entirety by reference for all purposes.

For the analytical instrument of the invention, it is sometimes desired to transfer fluids into and/or out of the substrate reservoir while the substrate is held within the instrument, and in particular while the substrate is held in optical alignment in the instrument, allowing for the reaction to be stopped, and in some cases, started again without moving the substrate. In some cases, the fluid is introduced and or removed from the substrate reservoir with a flow cell. The flow cell can transfer fluids into and/or out of the substrate reservoir, for example to or from other reservoirs. The flow cell transfers an appropriate amount of the inhibition agent into the substrate reservoir at a specified time in the process. The flow cell generally has valves that are controllable and a method of conveying the fluid, for example, by pressure, such that specified volumes of liquid are transferred into or out of the substrate reservoir at specified times. For example, in some cases, the flow cell is fluidically connected to an inhibitor reservoir that has an inhibition agent in it. In some cases the flow cell is fluidically connected to a release reservoir having an inhibitor release agent. The flow cell also can be connected to a volume into which liquids from the substrate reservoir are dispensed. For example, where reversible inhibitors are used, it can be desirable to exchange the volume within the substrate reservoir or flush the substrate reservoir to remove an inhibitor and re-introduce the reagents for the single molecule reaction.

The system for sequencing generally comprises a substrate having a plurality of single polymerase enzyme complexes each comprising a polymerase enzyme, a nucleic acid template, and a primer. The polymerase enzyme comprises a label having a signal that changes when the enzyme undergoes a conformational change. The substrate is in contact with sequencing reagents which provide the components required for the polymerase enzyme to add labeled nucleotides or nucleotide analogs while the addition of the nucleotide analogs is observed. The sequencing reagents include two or more types of nucleotides or nucleotide analogs, each nucleotide or nucleotide analog labeled with a different label. The polymerase sequentially adds nucleotides or nucleotide analogs to the growing strand, which extends from the primer. Each added nucleotide or nucleotide analog is complementary to the corresponding base on the template nucleic acid, such that the portion of the growing strand that is produced is complementary to the template.

The system comprises illumination optics for illuminating the enzyme complexes. The illumination optics illuminate the complexes in a wavelength range that will excite the labels on the nucleotides or nucleotide analog and which will excite the labels on the polymerase enzyme that are sensitive to changes in conformation.

The system further comprises detection optics for observing signals from the labeled nucleotides or nucleotide analogs and signals from the labeled enzyme during the enzyme mediated addition. The detection optics observe a plurality of single polymerase enzyme complexes concurrently, observing the nucleotide or nucleotide analog additions for each of them. For each of the observed polymerase enzyme complexes, the detection optics concurrently observe the signals from each of the labeled nucleotides or nucleotide analogs and the signals from the labeled enzyme that are indicative of enzyme conformation.

The system also comprise a computer configured to determine the type of the nucleotides or nucleotide analog that is added to the growing strand using the observed signal from the label of the nucleotide or nucleotide analogs; whereby observed signals from the labeled polymerase enzyme are used to indicate whether a type of nucleotide or nucleotide analog is incorporated into the growing strand. The computer generally receives information regarding the observed signals from the detection optics in the form of signal data. The computer stores, processes, and interprets the signal data, using the signal data in order to produce a sequence of base calls. The base calls represent the computers estimate of the sequence of the template from the signal data received combined with other information given to the computer to assist in the sequence determination. The computer combines the sticking data with the reaction data. The combining of this data can be done at various stages of the processing of the data from raw optical signals to called sequences. For example, in some cases, the combining involves filtering the reaction optical data using the sticking data to remove portions of the reaction optical data that correspond to sticking rather than to nucleotide analog incorporation. In other cases, the combining involves giving a statistical weight to the reaction data obtained in a given channel from a given optical confinement such that when the data is converted into base calls and combined with other data, the statistical weight provides an indication of whether to include or ignore some or all of the base calls from that that particular optical confinement, or to have data from another optical confinement take precedence.

Figure 11:
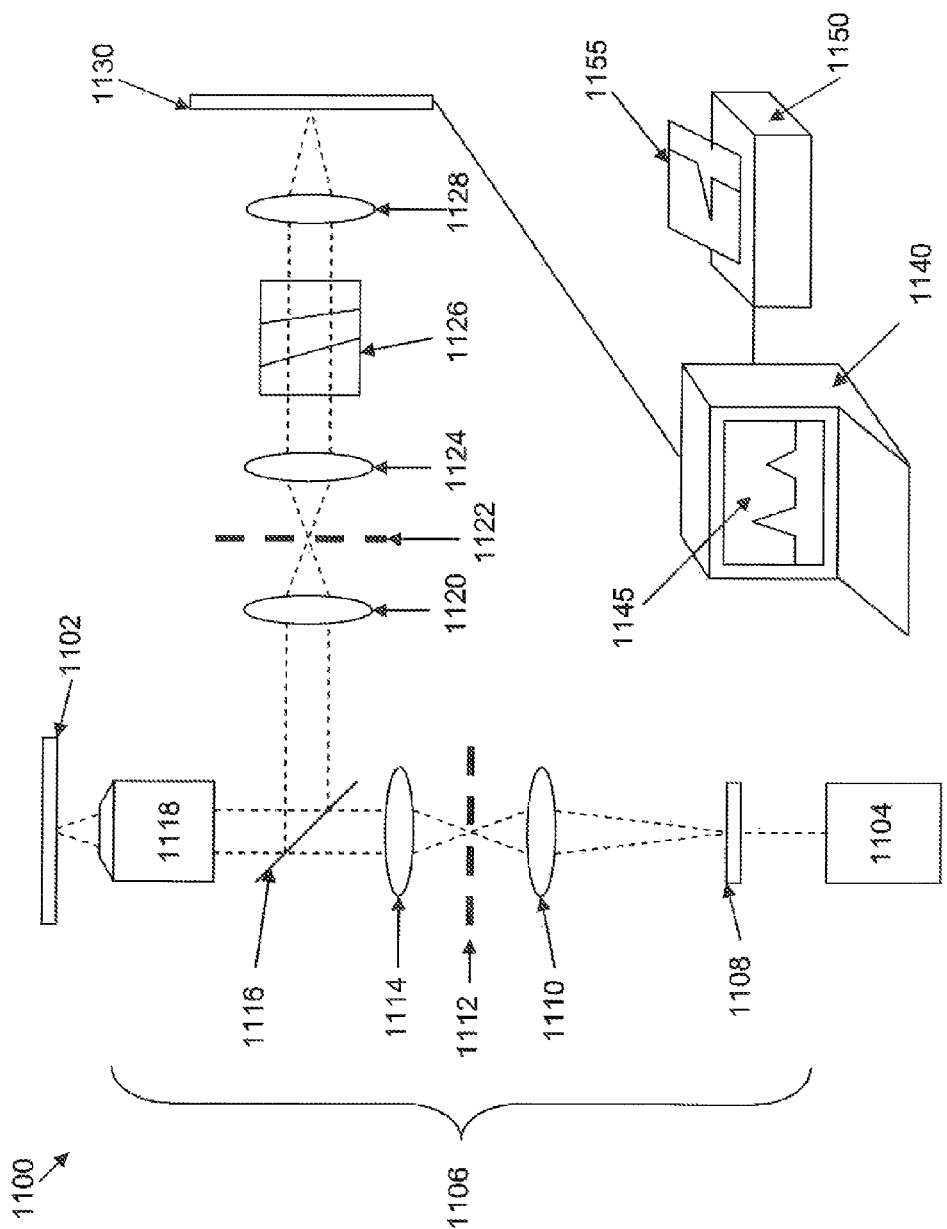
FIG. 11 is schematic illustration of a system of the invention.

One example of such system is illustrated in FIG. 11. As shown, the system 1100, includes a reaction array, such as a zero-mode waveguide array 1102 upon which a number of discrete reaction regions are arrayed. Within the zero-mode waveguides are immobilized single polymerase enzyme complexes having labels indicative of enzyme conformation. The zero-mode waveguides are also exposed to sequencing reagents including labeled nucleotides or nucleotide analogs, for example four differentially labeled nucleotides or nucleotide analogs. In the case of a zero mode waveguide array, large numbers of zero mode waveguides are typically provided arrayed in rows and columns on the substrate. Within the various ZMWs are provided reactants of interest for a given analysis. For example, in the context of nucleic acid sequencing by synthesis, a sequencing complex that includes a template nucleic acid sequence, a complementary primer sequence, a nucleic acid polymerase enzyme, and a reaction mixture of nucleotides or nucleotide analogs required for primer extension are provided with the ZMW. ZMW arrays can be fabricated at ultra high density, providing anywhere from 1100 ZMWs per $cm^2$, to 1,000,000 ZMWs per $cm^2$, or more. Thus, at any given time, it may be desirable to analyze the reactions occurring in from 100, 1000, 3000, 5000, 10,000, 20,000, 50,000, 100,000 or 1 Million, 10 Million or more ZMWs or other reaction regions within a single analytical system or even on a single substrate.

As shown, the system includes a source of excitation radiation for exciting fluorescent reactants in the reaction regions, such as laser 1104. An optical train 1106 delivers excitation radiation from laser 1104 to the ZMW array or substrate 1102. The optical train also collects fluorescent signals from the various ZMWs on the array, and conveys those signals to a detector, such as EMCCD 1130. The optical train 1106 includes a multiplex component, such as diffractive optical element (DOE) 1108 (also referred to as a holographic optical element or HOE), that converts a single excitation beam to large number of discrete excitation beams that will be targeted in an array of illumination spots that correspond to the location of the ZMWs on the array 1102. The multiple beams are passed through a dichroic 1116 that is selected to pass excitation light and reflect the fluorescence from the array 1102. Prior to passing through the dichroic 1116, the illumination beams may be passed through a confocal filter 1112 which may have associated with it a pair of focusing lenses, e.g., lenses 1110 and 1114, in order to focus these beams through the confocal pinhole(s). The excitation light that is passed through dichroic 1116 is then focused in a targeted pattern onto the plane of the array 1102 via objective lens 1118.

Fluorescent signals from array 1102 are then collected by the objective lens 1118, and passed to dichroic 1116, which reflects the fluorescent signals toward detector 1130. The signals from the discrete ZMWs on the array are then passed through a spatial filter, such as confocal mask 1122, to reduce background noise, such as photoluminescence, out of focal plane autofluorescence or scattered light, which again typically has associated with it a pair of focusing lenses, e.g., lenses 1120 and 1124. The signals can then be passed through a dispersive optical element, such as wedge prism 1126, that differentially directs light of differing spectral characteristics, allowing for distinction of different fluorescent signals based upon the location upon the detector, upon which they impinge. The differentially directed signal components are then directed through additional focusing optics, e.g., focusing lens 1128, and ultimately impact the EMCCD detector 1130. As noted, the position on the detector upon which a given signal is incident can then be indicative of (1) the originating ZMW in the array, and (2) the spectral characteristics of the signal component, which is used, for example, to identify the type of fluorescently labeled nucleotide analog incorporated in an extension reaction and that is used to monitor the label on the enzyme which is indicative of enzyme conformation. The signals are then detected by detector array 1130, and the data from that detection is transmitted to an appropriate data processing system, e.g., computer 1140, where the data is subjected to interpretation, analysis, and ultimately presented in a user ready format, e.g., on display 1145, or printout 1155, from printer 1150. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119, and U.S. patent application Ser. No. 11/901,273, all of which are incorporated herein by reference in their entireties for all purposes.).

Optical illumination and detections systems which can be used with the present invention are described, for example in U.S. patent application Ser. No. 12/351,173 filed Jan. 9, 2009, U.S. patent application Ser. No. 11/901,273 filed Sep. 14, 2007, U.S. patent application Ser. No. 12/151,979 filed May 9, 2008, U.S. patent application Ser. No. 12/079,944 filed Mar. 27, 2008, and U.S. patent application Ser. No. 11/849, 157 filed Aug. 31, 2007, which are incorporated herein by reference for all purposes.

Computers for use in carrying out the processes of the invention can range from personal computers such as PC or MacIntosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

We claim:

1. An analytical method comprising;
localizing a plurality of active molecules into optical confinements on a substrate whereby a plurality of the optical confinements comprise a single active molecule;
exposing the single active molecules in the optical confinements to a reagent solution, whereby either the single active molecules or a reagent in the reagent solution or both comprise one or more fluorescent labels;
initiating a reaction of the single active molecules;
measuring fluorescence from the plurality of optical confinements over time to monitor the reaction and to obtain reaction data from each of the plurality of confinements;
halting the reaction;
measuring fluorescence from the plurality of optical confinements over time while the reaction is halted to obtain sticking data; and
combining the sticking data with reaction data to provide a more accurate measurement of the reaction than if the sticking data was not used.

2. The method of claim 1 wherein the sticking data is used to determine a set of optical confinements that are most likely to provide accurate information about reaction.

3. The method of claim 1 wherein the active molecules comprise catalysts.

4. The method of claim 1 wherein the active molecules comprise enzymes.

5. The method of claim 4 wherein the enzymes comprise polymerases, reverse transcriptases, or ribosomes.

6. The method of claim 1 wherein pH, temperature, or light is used for halting of the reaction.

7. A method of improving accuracy in single molecule sequencing comprising:
   localizing a plurality of polymerase enzyme complexes into optical confinements whereby a plurality of the optical confinements comprise a single active polymerase enzyme complex;
   exposing the polymerase enzyme complexes to a reagent solution comprising the components necessary for polymerase activity including a plurality of types of labeled nucleotides or nucleotide analogs, each type comprising a different label;
   initiating a sequencing reaction;
   measuring fluorescence from the plurality of optical confinements over time during the sequencing reaction to obtain sequencing data;
   halting the sequencing reaction;
   measuring fluorescence from the plurality of optical confinements over time while the sequencing reaction is halted to obtain sticking data; and
   using both the sticking data and the sequencing data to provide sequencing information that is more accurate than if the sticking data was not used.

8. The method of claim 7 further comprising combining data from multiple optical confinements to produce combined sequencing data.

9. The method of claim 8 wherein the sticking data is used to determine a set of optical confinements that are least likely to provide accurate information about the reaction, and eliminating the sequencing data from these optical confinements in the combined sequencing data.

10. The method of claim 8 wherein the sticking data is used to determine a set of optical confinements that are most likely to provide accurate sequencing information and higher weight is given to the data from these optical confinements in producing the combined sequencing data.

11. The method of claim 7 wherein the sequencing data and sticking data comprise data from four or more optical channels, each corresponding to a label on a type of nucleotide or nucleotide analog.

12. The method of claim 11 wherein the sticking data in one channel, two channels, three channels, or in four channels is used to improve the accuracy of sequencing information in that channel or set of channels.

13. The method of claim 7 further comprising, after halting the reaction to obtain sticking data, initiating the reaction again and measuring fluorescence from the plurality of optical confinements over time during the ensuing sequencing reaction to obtain subsequent sequencing data, and using the subsequent sequencing data along with the sticking data and the sequencing data to provide sequencing information.

14. The method of claim 7 wherein each polymerase enzyme complex comprises a nucleic acid template.

15. The method of claim 14 wherein the nucleic acid template comprises DNA or RNA.

16. The method of claim 14 wherein the nucleic acid template is derived from genomic DNA, BACs, cDNA libraries, or PCR products.

17. The method of claim 7 wherein halting the sequencing reaction comprises inhibiting the polymerase enzyme.

18. The method of claim 17 wherein the polymerase enzyme is inhibited by the addition of a polymerase enzyme inhibitor.

19. The method of claim 18 wherein the polymerase enzyme inhibitor comprises a reversible inhibitor.

20. The method of claim 18 wherein the polymerase enzyme inhibitor comprises an irreversible inhibitor.

21. The method of claim 7 wherein halting the sequencing reaction comprises denaturing or degrading the polymerase enzyme.

22. The method of claim 7 wherein halting the sequencing reaction comprises changing the pH, changing the temperature, irradiating the enzyme with electromagnetic radiation, or adding a chelating agent.

* * * * *